United States Patent
Dahmani et al.

(10) Patent No.: US 12,057,207 B2
(45) Date of Patent: Aug. 6, 2024

(54) COMMUNICATION AND TRACKING SYSTEM FOR DISPOSABLE DRUG DELIVERY DEVICES

(71) Applicant: QuiO Technologies LLC, New York, NY (US)

(72) Inventors: Alexander Dahmani, New York, NY (US); Jared Schwartzentruber, Astoria, NY (US)

(73) Assignee: QuiO Technologies LLC, New York, NY (US)

( * ) Notice: Subject to any disclaimer, the term of this patent is extended or adjusted under 35 U.S.C. 154(b) by 676 days.

(21) Appl. No.: 16/466,725

(22) PCT Filed: Nov. 28, 2017

(86) PCT No.: PCT/US2017/063401
§ 371 (c)(1),
(2) Date: Jun. 5, 2019

(87) PCT Pub. No.: WO2018/106475
PCT Pub. Date: Jun. 14, 2018

(65) Prior Publication Data
US 2019/0295707 A1   Sep. 26, 2019

Related U.S. Application Data

(60) Provisional application No. 62/430,148, filed on Dec. 5, 2016.

(51) Int. Cl.
*G16H 20/13* (2018.01)
*G06K 19/07* (2006.01)
*H04L 65/40* (2022.01)
*H04L 67/12* (2022.01)
*H04W 64/00* (2009.01)

(52) U.S. Cl.
CPC ............. *G16H 20/13* (2018.01); *H04L 65/40* (2013.01); *G06K 19/0723* (2013.01); *H04L 67/12* (2013.01); *H04W 64/00* (2013.01)

(58) Field of Classification Search
CPC .......... G16H 20/13; H04L 65/40; H04L 67/12
See application file for complete search history.

(56) References Cited

U.S. PATENT DOCUMENTS

| | | | |
|---|---|---|---|
| 5,651,775 A * | 7/1997 | Walker | A61M 5/31533 604/207 |
| 8,212,677 B2 | 7/2012 | Ferguson | |
| 9,550,031 B2 | 1/2017 | Van Sickle et al. | |
| 9,692,829 B2 | 6/2017 | Starr et al. | |
| 10,220,166 B2 * | 3/2019 | Van Sickle | A61M 15/00 |

(Continued)

FOREIGN PATENT DOCUMENTS

WO   2015187793 A1   12/2015

OTHER PUBLICATIONS

International Search Report and Written Opinion dated Feb. 13, 2018 for International Application No. PCT/US17/63401.

*Primary Examiner* — Rajesh Khattar
*Assistant Examiner* — Steven G. S. Sanghera
(74) *Attorney, Agent, or Firm* — McDonnell Boehnen Hulbert & Berghoff LLP

(57) ABSTRACT

A communication and tracking system for disposable drug delivery devices and associated assemblies, systems, and methods are disclosed herein.

16 Claims, 13 Drawing Sheets

(56) References Cited

U.S. PATENT DOCUMENTS

| | | | |
|---|---|---|---|
| 2009/0012820 A1* | 1/2009 | Bishop | G16H 20/10 |
| | | | 705/3 |
| 2011/0112474 A1* | 5/2011 | Bochenko | A61M 39/02 |
| | | | 604/68 |
| 2011/0295215 A1* | 12/2011 | Nielsen | G16H 20/17 |
| | | | 604/257 |
| 2013/0282401 A1* | 10/2013 | Summers | G06Q 10/0833 |
| | | | 705/3 |
| 2014/0266785 A1 | 9/2014 | Miller | |
| 2014/0379874 A1* | 12/2014 | Starr | A61M 5/20 |
| | | | 709/219 |
| 2015/0174348 A1* | 6/2015 | Tunnell | A61M 15/0021 |
| | | | 128/200.14 |
| 2017/0189621 A1* | 7/2017 | Rodiera Olivé | A61M 39/0247 |
| 2018/0193564 A1* | 7/2018 | Dahmani | A61M 5/315 |

* cited by examiner

COMMUNICATION AND TRACKING SYSTEM FOR DISPOSABLE DRUG DELIVERY DEVICES

PRIORITY CLAIM

This application is a 371 U.S. National Stage application of International Application No. PCT/US2017/063401, filed on Nov. 28, 2017, which claims priority to U.S. Provisional Patent Application Ser. No. 62/430,148 which was filed on Dec. 5, 2016, their entire contents are incorporated herein by reference and relied upon.

TECHNICAL FIELD

The present technology relates generally to a communication and tracking system for disposable drug delivery devices. In particular, several embodiments are directed to a semi-reusable medicament assembly that includes a reusable electronic module operatively coupled to a disposable drug delivery device.

BACKGROUND

Parenteral medicaments are typically administered using a drug delivery device, such as an inhaler or auto-injector. In order to reduce the number of steps required to administer a dose, many parenteral medicaments are packaged in a disposable drug delivery that arrives pre-filled to a patient. This can prevent handling and dosing errors, and reduce the overall burden on the patient compared to reusable devices that must be properly loaded with the medicament prior to dosing. Disposable drug delivery devices have become much more popular than reusable devices because of their simplicity and ease-of-use. However, disposable devices must be inexpensive in order to be economically viable for patients and pharmaceutical companies to adopt. For this reason, disposable devices currently lack advanced functionalities that reusable devices enjoy, such as digital interfaces and reminder functions.

One important functionality that can been integrated into a drug delivery device is dose logging, where information about an administered dose is recorded by the device. Another important functionality is wireless connectivity, which enables data collected during a dosing event to be shared with loved ones or care providers. Together, these functionalities enable remote monitoring of treatment regimens and targeted support of patients, leading to greater medication adherence and improved medical outcomes. Based on these benefits, reusable devices have been developed with dose logging and wireless connectivity capabilities, an example of which includes the BETACONNECT™ available from Bayer (see www.betaseron.com/experience-betacconect for more information).

Recently, there have been attempts to introduce advanced functionalities into disposable drug delivery devices. The Alubena™ concept has been introduced by SHL Group (Sweden) for their disposable auto-injector devices. The concept consists of a reusable 'recording unit' with dose logging and digital feedback capabilities. The device also has Bluetooth connectivity for wirelessly transmitting data when synced to a companion application on a patient's smartphone. Comparable add-on sensors with Bluetooth connectivity have been introduced for disposable inhalers as well. The problem with these solutions is that the patient now must attach the add-on recording unit to each disposable drug delivery device before use, and must remove the recording unit prior to disposing of the delivery device. The YpsoMate® Smart concept has been introduced by Ypsomed (Switzerland), and overcomes the need for an add-on unit by integrating sensors and a near field communication (NFC) tag directly into the disposable auto-injector. However, the patient must place their smartphone close to the auto-injector and use a companion app to scan the NFC tag before and after the injection in order to record a dosing event. Both of these solutions burden the patient with additional steps, nullifying the benefits that a disposable drug delivery device is meant to offer. They also require the patient to own and properly operate a smartphone for the data sharing to work, which limits their applicability in important healthcare populations such as the elderly.

Therefore, a need exists for a solution that provides advanced features possible with reusable drug delivery devices, while preserving the simplicity and ease-of-use provided by disposable drug delivery devices.

SUMMARY

It is an object of the present disclosure to provide a system that wirelessly communicates with disposable drug delivery devices without any input from a patient.

In some embodiments, the present disclosure provides a communication and tracking system for a drug delivery device including one or more servers having one or more processors configured to receive medicament information about a medicament in the drug delivery device at or after a point of production of the drug delivery device. The one or more processors of the one or more servers are further configured to receive identification information of the drug delivery device. The one or more processors of the one or more servers are further configured to link the identification information and the medicament information to a medicament assembly record. The one or more processors of the one or more servers are further configured to receive dispensation information that indicates that the drug delivery device has been dispensed to a patient. The communication and tracking system for a drug delivery device further includes a drug delivery device having one or more processors configured to determine that the drug delivery device has been removed from a packaging of the drug delivery device based on a first signal from at least one activation sensor. The one or more processors of the drug delivery device are further configured to activate, in response to the determination that the drug delivery device has been removed from the packaging, at least one performance sensor configured to indicate a dosing event of the drug delivery device. The one or more processors of the drug delivery device are further configured to determine, based on a second signal from the at least one performance sensor, that the dosing event of the drug delivery device has occurred. The one or more processors of the drug delivery device are further configured to send drug delivery performance information comprising information that the dosing event has occurred to the one or more servers. The drug delivery performance information is sent via a long range wireless network.

In some embodiments, the present disclosure provides a drug delivery apparatus including at least one activation sensor, at least one performance sensor configured to indicate a dosing event of the drug delivery device, a memory, and one or more processors coupled to the memory. The one or more processors are configured to determine that the drug delivery device has been removed from a packaging of the drug delivery device based on a first signal from the at least one activation sensor. The one or more processors are further configured to activate, in response to the determination that the drug delivery device has been removed from the packaging, the at least one performance sensor. The one or more processors are further configured to determine based on a second signal from the at least one performance sensor, that a dosing event of the drug delivery device has occurred. The one or more processors are further configured to send drug delivery performance information comprising information that the dosing event has occurred to a server. The drug delivery performance information is sent via a long range wireless network.

In some embodiments, the present disclosure provides a non-transitory computer readable medium having instructions stored thereon that, upon execution by a computing device, cause the computing device to perform operations including receiving medicament information about a medicament in the drug delivery device at or after a point of production of the drug delivery device. The operations further include receiving identification information of the drug delivery device. The operations further include linking the identification information and the medicament information to a medicament assembly record. The operations further include receiving dispensation information that indicates that the drug delivery device has been dispensed to a patient. The operations further include receiving drug delivery performance information comprising information that a dosing event of the drug delivery device has occurred. The drug delivery performance information is received via a long range wireless network.

In some embodiments, the present disclosure provides a communication and tracking system for disposable drug delivery devices. The communication and tracking system comprises: a semi-reusable medicament assembly, the semi-reusable medicament assembly comprising a disposable drug delivery device and a reusable electronic module operatively coupled with the disposable drug delivery device; and a centralized system remote from the semi-reusable medicament assembly, the centralized system including at least one processor, wherein the centralized system is configured to receive, from one or more information sources, and store information related to the semi-reusable medicament assembly.

The semi-reusable medicament assembly may be configured to communicate with the centralized system via at least one wireless network, such as a cellular network. The one or more information sources may include at least one of (i) a point of production of the semi-reusable medicament assembly, (ii) a point of distribution of the semi-reusable medicament assembly, (iii) a point of dispensation of the semi-reusable medicament assembly, and (iv) the reusable electronic module. The centralized system may include a central database, and the information received from the one or more information sources may be stored in the central database. The centralized system may be configured to create a medicament assembly record in the central database based on information identifying the semi-reusable medicament assembly.

Further, the centralized system may be configured to receive information identifying a patient associated with the semi-reusable medicament assembly when the semi-reusable medicament assembly is dispensed, and associate the medicament assembly record with an identity of the patient. Additionally, the reusable electronic module may be configured to collect information regarding a use of the disposable drug delivery device, such as a drug delivery performance information, and to wirelessly communicate at least a portion of the drug delivery performance information to the centralized system after a dosing event.

In some embodiments, the present disclosure provides a semi-reusable medicament assembly comprising: a disposable drug delivery device comprising a primary container filled with a medicament and a drive mechanism for delivering the medicament into a user; a reusable electronic module comprising one or more engagement features configured to operatively couple with at least one of (i) one or more mechanical features of the disposable drug delivery device and (ii) one or more electrical features of the disposable drug delivery device; a trigger for the user to activate the drive mechanism; a power source configured to provide power to the reusable electronic module; and one or more sensors configured to capture a drug delivery performance information of the disposable drug delivery device.

In some embodiments, the present disclosure provides a method for tracking disposable drug delivery devices, the method comprising: receiving, from one or more information sources, at a centralized system remote from at least one semi-reusable medicament assembly, information related to the semi-reusable medicament assembly; and storing, by the centralized system, the information related to the semi-reusable medicament assembly, wherein the centralized system includes at least one processor, and wherein the semi-reusable medicament assembly comprises a disposable drug delivery device and a reusable electronic module operatively coupled with the disposable drug delivery device.

In some embodiments, the present disclosure provides another method for tracking disposable drug delivery devices, the method comprising creating, by at least one processor, a medicament assembly record for a given semi-reusable medicament assembly in a central database remote from the given semi-reusable medicament assembly, wherein the given semi-reusable medicament assembly comprises a disposable drug delivery device and a reusable electronic module operatively coupled with the disposable drug delivery device, and wherein the medicament assembly record includes at least first information associating the disposable drug delivery device with the reusable electronic module.

In some embodiments, the present disclosure provides a centralized system for tracking disposable drug delivery devices, the centralized system comprising: at least one processor; a memory coupled with the at least one processor; and program instructions that are stored in the memory and, when executed by the at least one processor, cause the at least one processor to receive, from one or more information sources, and store information related to at least one semi-reusable medicament assembly, the semi-reusable medicament assembly comprising a disposable drug delivery device and a reusable electronic module operatively coupled with the disposable drug delivery device.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. For ease of reference, throughout this disclosure identical reference numbers may be used to identify identical or at least generally similar or analogous components or features.

DETAILED DESCRIPTION

Specific details of several embodiments of the technology are described below with reference to FIGS. 1-11. Although many of the embodiments are described below with respect to devices, systems, and methods for tracking distribution and use of disposable drug delivery devices, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1A-11.

Examples of Semi-Reusable Medicament Assembly and Related Devices

Figure 1A:
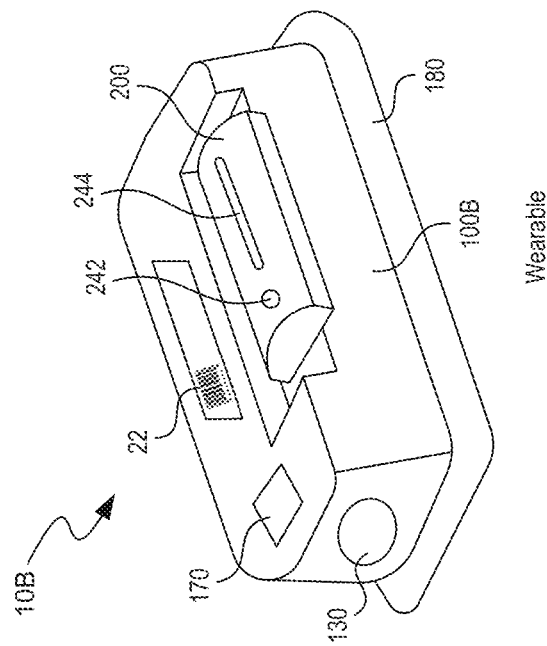
FIGS. 1A and 1B show handheld and wearable semi-reusable medicament assemblies with and without a reusable electronic module operatively connected to the disposable drug delivery device, respectively, in accordance with an embodiment of the present technology.
Figure 1A:
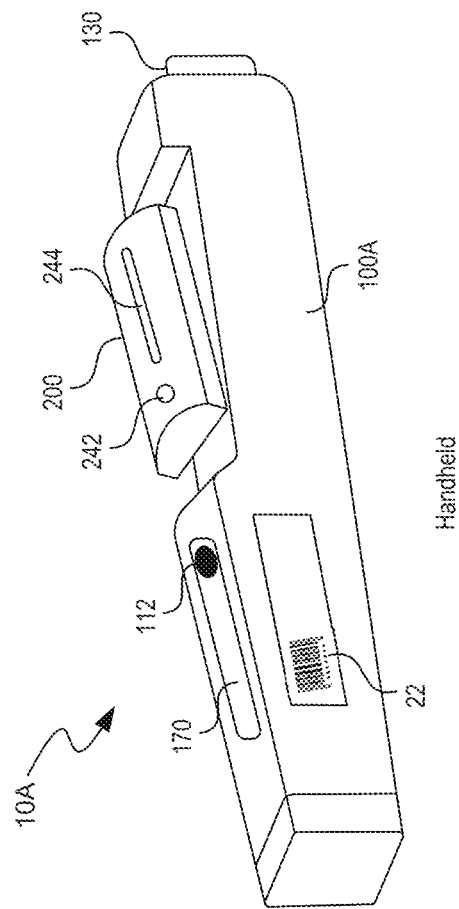
Figure 1B:
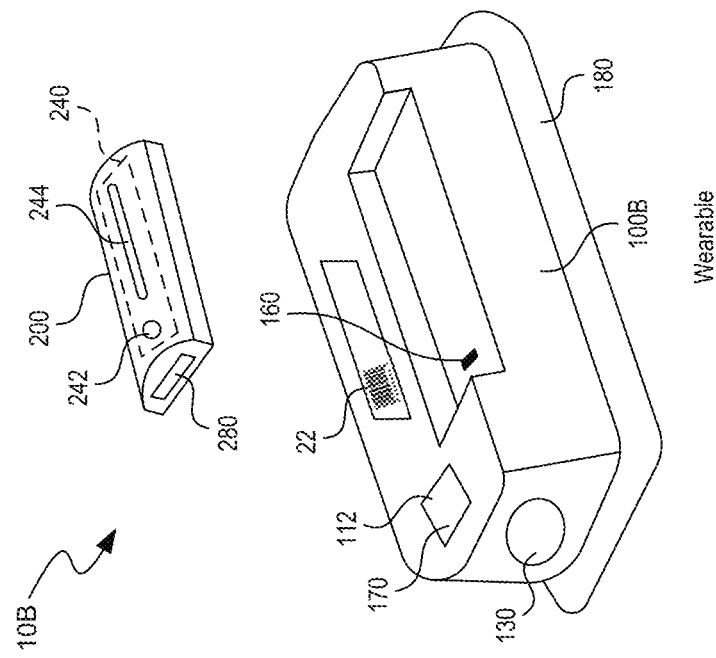
Figure 1B:
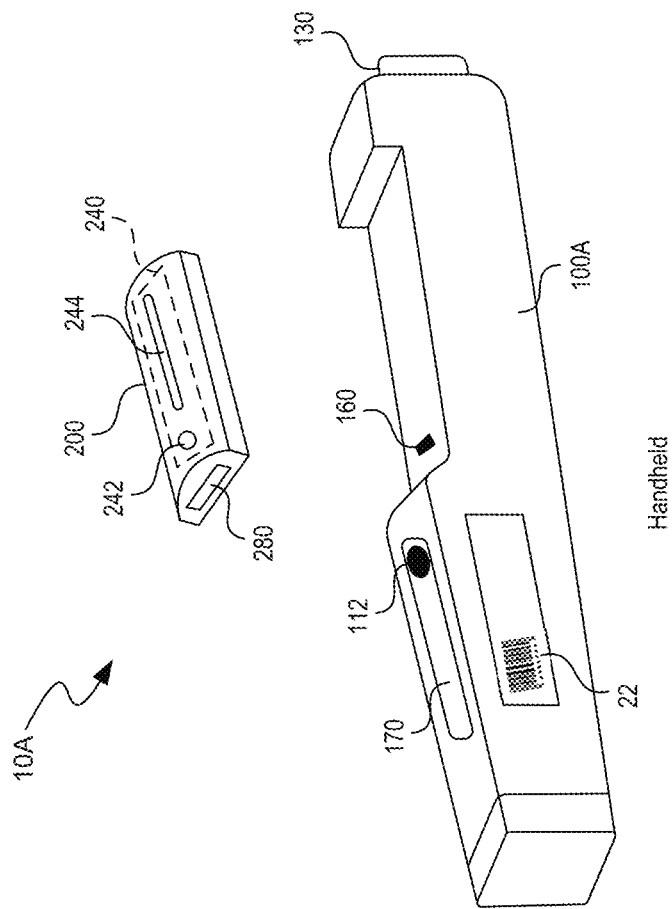

FIGS. 1A and 1B show semi-reusable medicament assemblies 10A and 10B with and without a reusable electronic module 200, respectively, in accordance with an embodiment of the present technology. As shown in FIG. 1A, the reusable electronic module 200 may be operatively coupled to a disposable drug delivery device, which may be a handheld-type disposable drug delivery device or a wearable-type disposable drug delivery device. In particular, as shown, the semi-reusable medicament assembly 10A includes a handheld disposable drug delivery device 100A and the semi-reusable medicament assembly 10A includes a wearable disposable drug delivery device 100B. In some embodiments, the electronic module 200 connects to an outer surface of the drug delivery device 100A, 100B. In other embodiments, the electronic module 200 is installed within a shell of the drug delivery device 100A, 100B. In various embodiments, the disposable drug delivery device 100A, 100B contains a medicament 112, a medicament viewing window 170, and a medicament label 22. In one embodiment, the medicament label 22 includes information readable by a user, such as a patient, as well as by a machine. In certain embodiments, the drug delivery device 100A, 100B includes a start switch (not shown) for initiating a delivery of the medicament 112 into the user. In various embodiments, as shown in FIG. 1B, the reusable electronic module 200 comprises a user interface 240 for providing feedback to the patient. In certain embodiments, the user interface 240 includes a device status indicator 242 and a drug delivery status indicator 244.

Referring to FIG. 1B, the reusable electronic module 200 further comprises one or more engagement features 280 that can connect to the disposable drug delivery device 100A, 100B. In some embodiments, the engagement features 280 form mechanical and electrical connections when the reusable electronic module 200 is properly attached to the disposable drug delivery device 100A, 100B. In certain embodiments, the disposable drug delivery device 100A, 100B includes a stopping feature 160 through which the reusable electronic module 200 can physically interrupt the drug delivery process.

As noted above, the disposable drug delivery device included in the semi-reusable medicament assembly may be a handheld-type disposable drug delivery device or a wearable-type disposable drug delivery device. In certain embodiments, the reusable electronic module 200 is identical across distinct types of the disposable drug delivery device. In various embodiments, the semi-reusable medicament assembly 10A comprises the handheld drug delivery device 100A for administering low-volume doses of the medicament 112. In some embodiments, the semi-reusable medicament assembly 10B comprises the wearable disposable drug delivery device 100B for administering high-volume doses of medicament 112. In one embodiment, the wearable drug delivery device 100B has an adhesive surface 180 for attaching to a skin of the user and administering the medicament 112 over an extended period of time.

In various embodiments, a drug delivery device may include an integral electronic module. That is, the electronic module is not easily separable from the drug delivery device. In such embodiments, the entire drug delivery device, including the electronic module, may be disposable. Even where an electronic module is separable from a drug delivery device, the electronic module may be disposable. In other words, in some embodiments, an electronic module may be configured to be disposed of after being used with a single drug delivery device.

Figure 2:
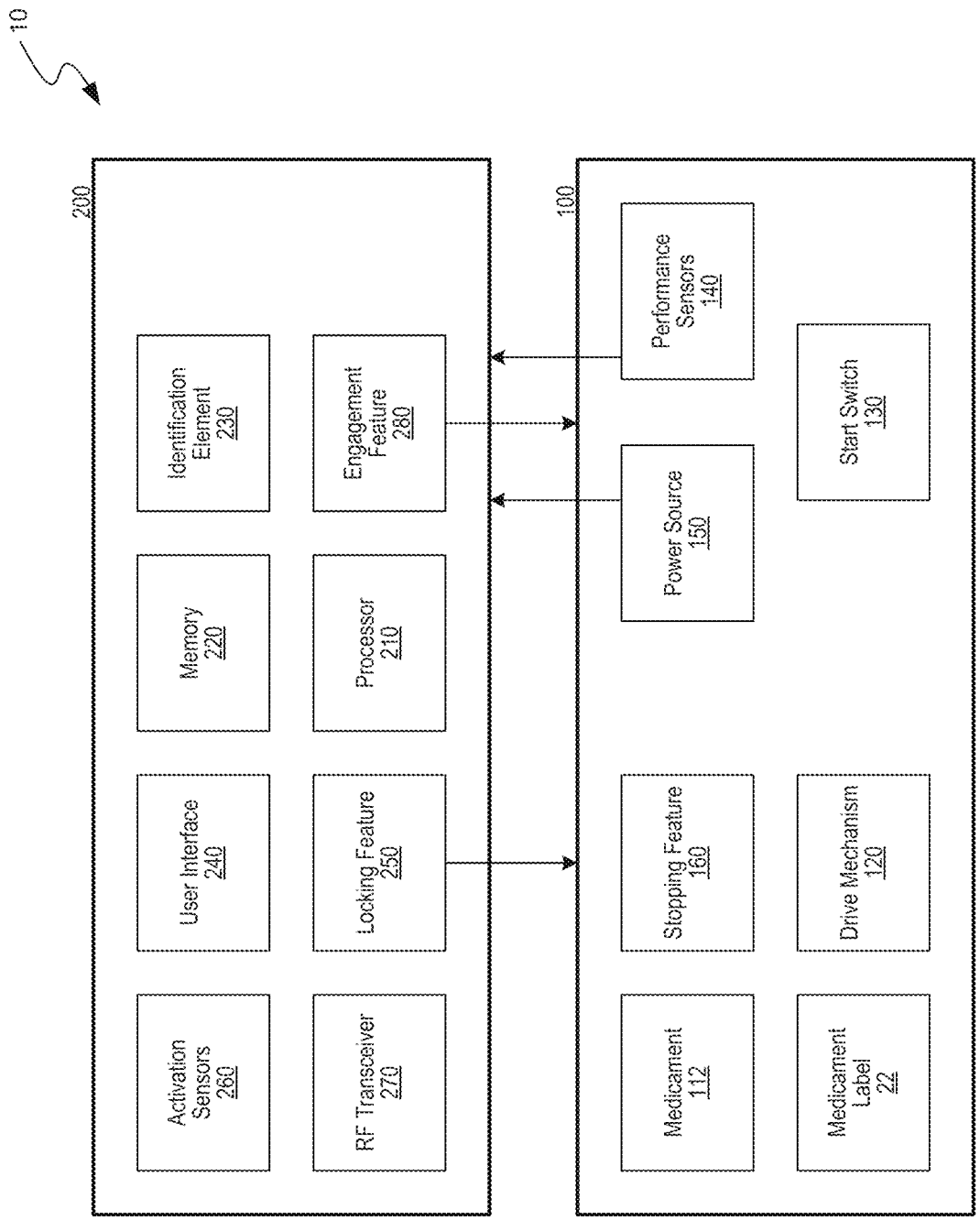
FIG. 2 is a block diagram illustrating in more detail components of a semi-reusable medicament, in accordance with an embodiment of the present technology.

FIG. 2 is a block diagram illustrating in more detail components of a semi-reusable medicament assembly 10, in accordance with an embodiment of the present technology. The semi-reusable medicament assembly 10 comprises the reusable electronic module 200 operatively coupled to a disposable drug delivery device 100. The semi-reusable medicament assembly 10 may be either the handheld-type semi-reusable medicament assembly 10A or the wearable-type semi-reusable medicament assembly 10B. Accordingly, the disposable drug delivery device 100 may be either the handheld disposable drug delivery device 100A or the disposable drug delivery device 100B.

In various embodiments, the disposable drug delivery device comprises the medicament 112, a drive mechanism 120 for delivering the medicament 112 into a user (e.g., a patient), a start switch 130 for the user to active the drive mechanism 120, and performance sensors 140 for recording information related to the performance of a dosing event. In certain embodiments, the disposable drug delivery device 100 further comprises a power source 150 for providing power to electrical components contained within the operatively coupled electronic module 200. In one embodiment, the power source 150 is a battery.

In various embodiments, the electronic module 200 comprises the user interface 240, a memory 220, one or more activation sensors 260, and a processor 210 for controlling components and controlling/carrying out various functions of the semi-reusable medicament assembly 10 including those as described herein. In this regard, in some embodiments, the processor 210 is programmed to power on the semi-reusable electronic module 200 based on inputs from the activation sensors 260. In one embodiment, the activation sensors 260 include a light sensor, a temperature sensor, and an accelerometer.

In various embodiment, the activation sensors 260 are used to determine when to activate other aspects of an electronic module or drug delivery device. This can occur to help preserve a power source of the drug delivery device, such as a battery. For example, the activation sensor 260 is a light sensor and a packaging of the drug delivery device prevents some or all external light outside of the packaging from entering the packaging. Accordingly, once a user removes the drug delivery device from the packaging, a signal from the light sensor will sense light that the drug delivery device is now exposed to. This can indicate that the drug delivery device will be used soon. Accordingly, the device can activate, or begin monitoring, any various performance sensors included in the drug delivery device (and its associated electronic module) only after the activation sensors have indicated that the drug delivery device has been removed from the packaging. A light sensor may be any of various types of sensors, such as proximity or depth sensors, and light sensors that sense various types of light including infrared and visible light sensors.

This may be particularly valuable where the power source does not store a lot of power. By only monitoring performance sensors for a relatively short amount of time after the drug delivery device is removed from the packaging, a smaller and cheaper power source may be utilized. A typical drug delivery device spends much more time (orders of magnitude more time) being transported, stored, etc. than it does after being removed from the packaging and before a dosing event.

In other examples, different or additional sensors than a light sensor may be used to determine that the drug delivery device has been removed from its packaging. For example, an accelerometer may be used to identify patterns of motion and acceleration typical with a drug delivery device being handled by a user and/or taken out of its packaging. A signature of movement typical of being handled or removed from packaging can also trigger activation of the performance sensors. In some embodiments, multiple sensors may be used. For example, a light sensor and an accelerometer may be required to be activated or register a signal before the performance sensors are activated/monitored. In another example, the activation sensors may operate in a multi-level logic pattern. For example, an accelerometer may be monitored for motion to determine when a drug delivery device is being handled. When a signal is received indicating that movement, monitoring of a light sensor may begin to determine if the drug delivery device has been removed from its packaging. Only after both of these have been determined, will the performance sensors be monitored/activated.

In various embodiments, a temperature sensor may also be used, either alone or in combination with the other sensors indicated herein. For example a temperature sensor may be used in drug delivery devices in which the medicament stored therein is supposed to be stored at a particular temperature or temperature range. For example, some medicaments need to be refrigerated. In order to determine that the drug delivery device is about to be used, necessitating activation of the performance sensors, the temperature sensor may be monitored for a rise in temperature. Such monitoring may be done concurrent with other sensors (e.g., an accelerometer, a light sensor) or may be done in a multi-level logic pattern as disclosed herein.

Additionally, a wireless transceiver of the drug delivery device may be activated only after it is determined that a dosing event has occurred. This can similarly save power, allowing for a smaller and cheaper power source to be used.

The processor 210 may be programmed with suitable processor-executable program instructions (e.g., machine-readable instructions and/or other suitable (e.g., higher-level) programming instructions) that may be stored in the memory 220 or another data storage associated with the processor 210. In general, the processor 220 may be any suitable type of a processing unit, such as a dedicated processor or a general purpose processor. In one embodiment, the processor 220 is a microcontroller.

In certain embodiments, the drug delivery device 100 includes the medicament label 22 and the electronic module 200 includes an identification element 230 ("ID element"). In one embodiment, the identification element 230 is an RFID tag. In some embodiments, the electronic module 200 further comprises the one or more engagement features 280. In certain embodiments, the engagement features 280 form an electrical connection with the power source 150 and the performance sensors 140 in the drug delivery device 100. In such embodiments, power is delivered to the components in the electronic module 200 through the engagement features 280. In certain embodiments, the processor 210 collects information from the performance sensors 140 while the drive mechanism 120 is delivering the medicament 112. In one embodiment, the processor 210 stores the information from the performance sensors 140 in the memory 220.

As further shown in FIG. 2, the electronic module 200 includes an RF transceiver 270. In certain embodiments, the processor 210 causes the RF transceiver 270, such as by sending suitable control signals(s), to wirelessly transmit the information from the performance sensors 140 using the RF transceiver 270 to a remote system, as will be described later. In certain embodiments, the electronic module 200 further comprises a locking feature 250 that physically interacts with a stopping feature 160 contained in the drug delivery device 100. In such embodiments, the stopping feature 160 can be moved by the locking feature 250 to impede the movement of the drive mechanism 120. In one embodiment, the locking feature 250 is controlled by the processor 210.

The performance sensors 140 may be a variety of types of sensors, such as a pressure sensor, a vibration or acoustic sensor, a light or proximity sensor, or a flow sensor. For example, these sensors may monitor the medicament in the drug delivery device to determine when it has been delivered during a dosing event. In some embodiments, a vibration or acoustic sensor may be used to listen or sense when mechanical aspects of the drug delivery device have actuated to deliver the medicament stored therein. For example, the mechanical aspects of the drug delivery device may be configured to click or vibrate when a dosing event occurs. A flow sensor may determine that medicament has been dispensed and/or how much medicament has been dispensed. A portion of the drug delivery device that stores the medicament may be transparent or partially transparent, allowing a light or proximity sensor to monitor the medicament and used to determine if, when, and/or how much medicament is dispensed. As disclosed herein, in some embodiments, the performance sensors may be activated and/or monitored only after the drug delivery device is removed from the packaging.

Figure 3:
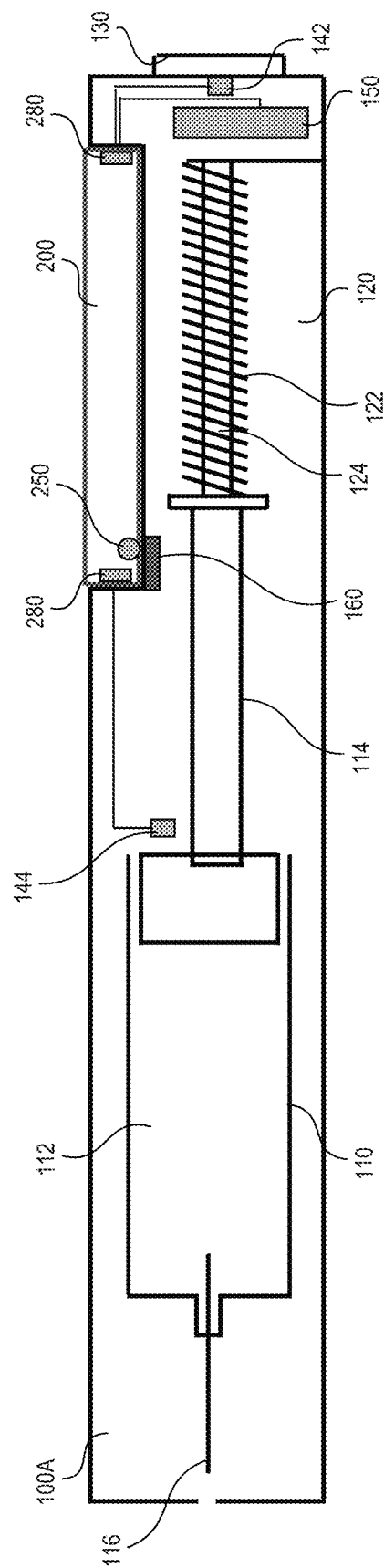
FIG. 3 is a cross-sectional perspective view of the semi-reusable medicament assembly of FIGS. 1A and 1B, in accordance with an embodiment of the present technology.

FIG. 3 is a cross-sectional perspective view of the handheld semi-reusable medicament assembly 10A of FIGS. 1A and 1B, in accordance with an embodiment of the present technology. In one embodiment, the handheld disposable drug delivery device 100A contains multiple doses of the medicament 112. In another embodiment, the handheld disposable drug delivery device 100A can only be used once and contains enough of the medicament 112 for a single dosing event. In various embodiments, the handheld disposable drug delivery device 100A is an injection device for subcutaneous administration of the medicament 112. In some embodiments, the handheld disposable drug delivery device 100A comprises a primary container 110 housing the medicament 112. In one embodiment, a needle 116 is attached to the primary container 110 for the medicament 112 to flow through. In some embodiments, the drive mechanism 120 is coupled to the primary container 110 through a plunger 114. In certain embodiments, the drive mechanism 120 comprises a spring 122 attached to a drive rod 124. In one embodiment, the drive rod 124 is coupled to the plunger 114, such that the decompression of the spring 122 delivers a force through the drive rod 124, driving the plunger 114 into the primary container 110 and pushing the medicament 112 out through the needle 116.

Referring back to FIG. 3, the drive mechanism 120 is activated by a start switch 130 located on a surface of the handheld disposable drug delivery device 100A. In certain embodiments, a forward movement of the drive mechanism 120 can be prevented by an activation of the stopping feature 160. In some embodiment, the stopping feature 160 is activated by the locking feature 250 housed in the operatively coupled electronic module 200. As explained above, the electronic module 200 includes the engagement features 280 that physically interface with the drug delivery device 100, such the handheld disposable drug delivery device 100A. In certain embodiments, the engagement features 280 connect to performance sensors 140 contained within the handheld disposable drug delivery device 100A. In one embodiment, the performance sensors 140 include an initiation sensor 142 for detecting pressure on the start switch 130 sufficient to activate the drive mechanism 120.

In one embodiment, the performance sensors 140 further include a completion sensor 144 for detecting when the drive mechanism 120 reaches its most distal position upon completion of a dosing event. In some embodiments, the performance sensors 140 communicate information to the reusable electronic module 200 through the engagement features 280. In certain embodiments, the handheld disposable drug delivery device 100A further comprises the power source 150 configured to provide power to the electronic components of the semi-reusable medicament assembly 10A, including the performance sensors 140 and the locking feature 250.

Figure 4:
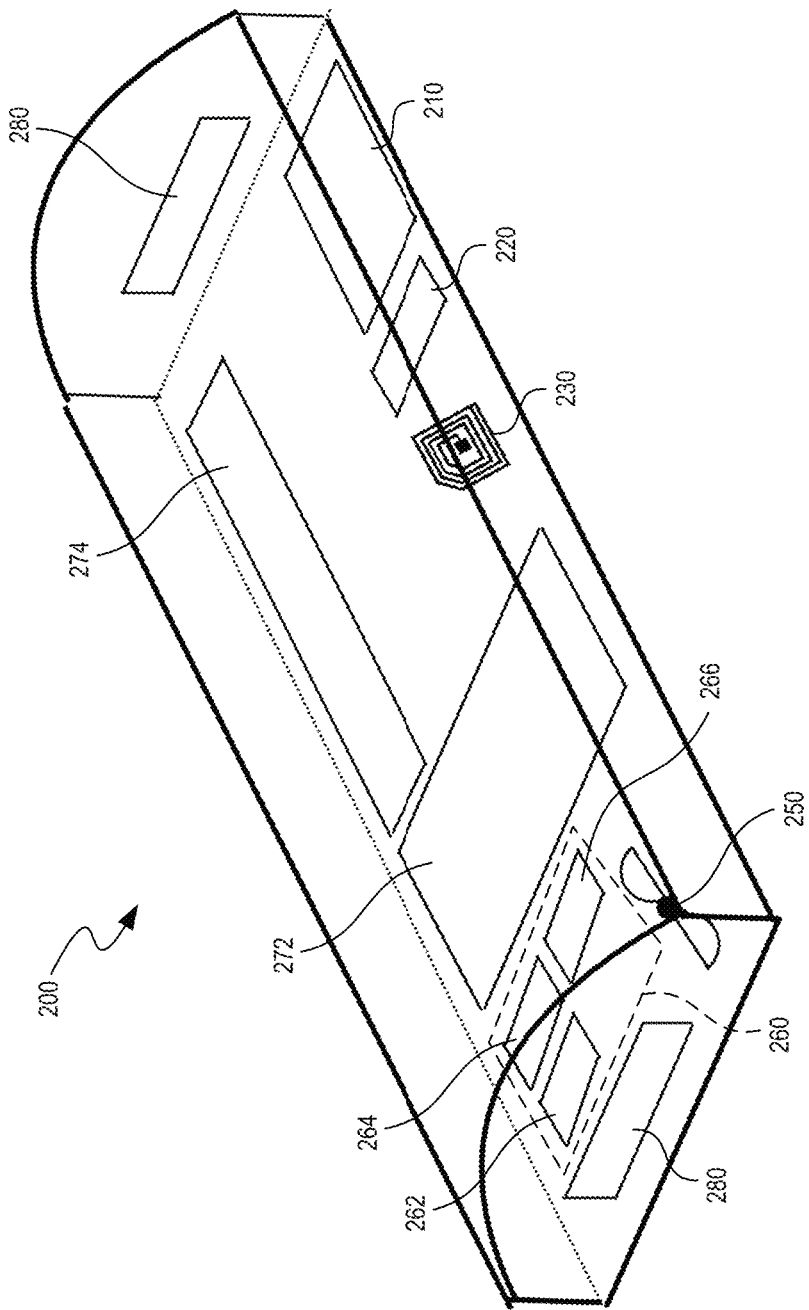
FIG. 4 is a cross-sectional perspective view of the reusable electronic module, in accordance with an embodiment of the present technology.

FIG. 4 is a cross-sectional perspective view of the reusable electronic module 200, in accordance with an embodiment of the present technology. As noted above in connection with FIG. 2, in certain embodiments, the reusable electronic module 200 comprises the one or more engagement features 280 on a surface of the shell. In certain embodiments, the engagement features 280 are designed to form mechanical and electrical connections with the drug delivery device 100. In one embodiment, the engagement features 280 are designed to operatively connect to multiple types of drug delivery device 100. In some embodiments, the reusable electronic module 200 further comprises the locking feature 250 positioned on an inner surface such that it can physically interact with the stopping feature 160 of an operatively coupled drug delivery device 100. In certain embodiments, the reusable electronic module 200 further comprises the one or more activation sensors 260 for powering on the electronic module 200 upon one or more signals. In one embodiment, the one or more activation sensors 260 include a light sensor 262, a temperature sensor 264, and an accelerometer 266.

With reference to FIG. 4, the reusable electronic module 200 also comprises the previously-noted machine-readable ID element 230, the RF transceiver 270, and the memory 220 for storing information. In general, the RF transceiver 270 comprises one or more RF transceivers that provide a wireless connectivity capability. In certain embodiments, the RF transceiver 270 enables the reusable electronic module 200 to establish a wireless connection with at least one wireless network that may interconnect the reusable electronic module 200 with other wired and/or wireless network(s) (e.g., the Internet, a local area network (LAN), etc.), system(s), and/or entitie(s), such as a remote computerized system that may include one or more servers (as will be described later). In one or more embodiments, the wireless network comprises a cellular network, and the reusable electronic module 200 is configured to wirelessly communicate (e.g., send and receive data) over the cellular network. Those skilled in the art will appreciate that cellular networks will typically include cellular data networks for carrying wireless data communications in addition to voice communications. A general architecture of various cellular data network technologies is understood in the art. Further, the cellular network may include networks deployed by one or more wireless carriers to provide the semi-reusable medicament assembly 10 with a cellular service/coverage in various geographic locations (e.g., a roaming service).

In this regard, in some embodiments, the RF transceiver 270 includes a cellular chip/chipset 272 and an antenna 274 adapted for wireless communication over the cellular network in accordance with one or more suitable communication protocols (e.g., Code Division Multiple Access (CDMA), Global System for Mobile Communications (GSM), Time Division Multiple Access (TDMA), General Packet Radio Service (GPRS), Long Term Evolution (LTE), and/or other(s)). In other embodiments, the RF transceiver 270 may be instead or in addition to configured for wireless communication via other suitable type(s) wireless network(s), some examples of which include a single wireless access point/router that may connect, e.g., to the Internet, a wireless local area network (WLAN) (e.g., an 802.11-based/Wi-Fi WLAN), a long-range Wi-Fi network, a WiMax network, and a satellite communication network.

To illustrate, the RF transceiver 270 may be configured such that the reusable electronic module 200 can wirelessly connect to a first wireless network (e.g., a cellular network) or a second wireless network (e.g., a Wi-Fi network or "hot spot"), depending, e.g., on a location of the reusable electronic module 200, availability of a cellular service, and/or other factor(s). As such, in certain embodiments, the reusable electronic module 200 can communicate data with another entity (e.g., a remote server connected to the Internet) via either the first wireless network or the second wireless network. In this regard, the RF transceiver 270 may comprise multiple transceivers operating in accordance with different communication protocols/standards. As an example, the RF transceiver 270 may include the cellular chipset 272, as noted above, as well as a wireless adapter for communications in accordance with a suitable WLAN standard (e.g., the IEEE 802.11x standard).

In certain embodiments, the information stored in the memory 220 is wirelessly received via the RF transceiver 270 or collected from sensors in the semi-reusable medicament assembly 10, including the one or more activation sensors 260 in the reusable electronic module 200 as well as the one or more performance sensors 140 in the disposable drug delivery device 100. FIG. 4 further shows the processor 220 that, as described previously, can control functions of the electronic components in the semi-reusable medicament assembly 10, including the locking feature 250, the one or more performance sensors 140, the one or more activation sensors 260, the RF transceiver 270, and the memory 220.

Referring to FIGS. 3 and 4, the reusable electronic module 200 and the disposable drug delivery device 100 function together during operation of the semi-reusable medicament assembly 10 by a user. In certain embodiments, the user interface 240 on the reusable electronic module 200 is configured to alert the user of the status of the delivery process based on information received from the performance sensors 140 in the disposable drug delivery device 100. In some embodiments, the user interface 240 alerts the user when the drug delivery process has begun and finished. In one embodiment, the user interface 240 alerts the user when an error occurs before, during, or after the drug delivery process.

In certain embodiments, the processor 210 will activate the locking feature 250 when the medicament 112 inside the disposable drug delivery device 100 is no longer safe to be administered. This may occur when the reusable medicament assembly 10 has been stored at an inappropriate temperature, or the medicament 112 has surpassed its expiration date. In certain embodiments, the memory 220 inside the reusable electronic module 200 is configured to store information collected during multiple dosing events. In some embodiments, the information collected by the reusable electronic module 200 during a dosing event includes a patient contact, a duration of the dosing event, an amount of medicament administered, a temperature of the assembly 10 during the dosing event, and a timestamp of the dosing event. In one embodiment, the information collected by the reusable electronic module 200 is calculated and analyzed on a remote computerized system (e.g., by one or more remote servers) following a wireless communication of a raw data from the module 200.

The reusable electronic module 200 and the disposable drug delivery device 100, as shown in FIGS. 1A-4, are designed for automated assembly and disassembly. This enables the reusable electronic module 200 to be processed and reused at scale, while each drug delivery device 100 is disposed of after the medicament 112 has been emptied and the reusable electronic module 200 has been separated.

In this regard, in certain embodiments, the reusable electronic module 200 is reversibly-attached to the disposable drug delivery device 100 using an adhesive. In one embodiment, the adhesive can be dissolved using a reagent or solution. In other embodiments, the reusable electronic module 200 is reversibly-attached to the disposable drug delivery device 100 using mechanical connectors, such as a latch. In one embodiment, the latch can only be released by using a special tool or machinery. The reusable electronic module 200 and the disposable drug delivery device 100 are designed to remain securely connected while possessed by a user. From the user's perspective, the semi-reusable medicament assembly 10 is a fully-disposable device used to deliver a medicament.

In summary, in some aspects, the present disclosure provides a semi-reusable medicament assembly that comprises: (i) a disposable drug delivery device comprising a primary container filled with a medicament and a drive mechanism for delivering the medicament into a user (e.g., a patient), (ii) a reusable electronic module comprising one or more engagement features configured to operatively couple with at least one of mechanical and/or electrical features of the disposable drug delivery device, (iii) a trigger for the user to activate the drive mechanism, (iv) a power source configured to provide power to the reusable electronic module, and (v) one or more sensors configured to capture drug delivery performance information of the disposable drug delivery device.

In some embodiments, the disposable drug delivery device 100 includes the medicament 112 in an amount of at least about 1 dose. In other embodiments, the device 100 includes the medicament 112 in an amount of at least 2 doses but no more than 20 doses. In yet other embodiments, the device 100 includes the medicament 112 in an amount of more than 20 doses.

Figure 5:
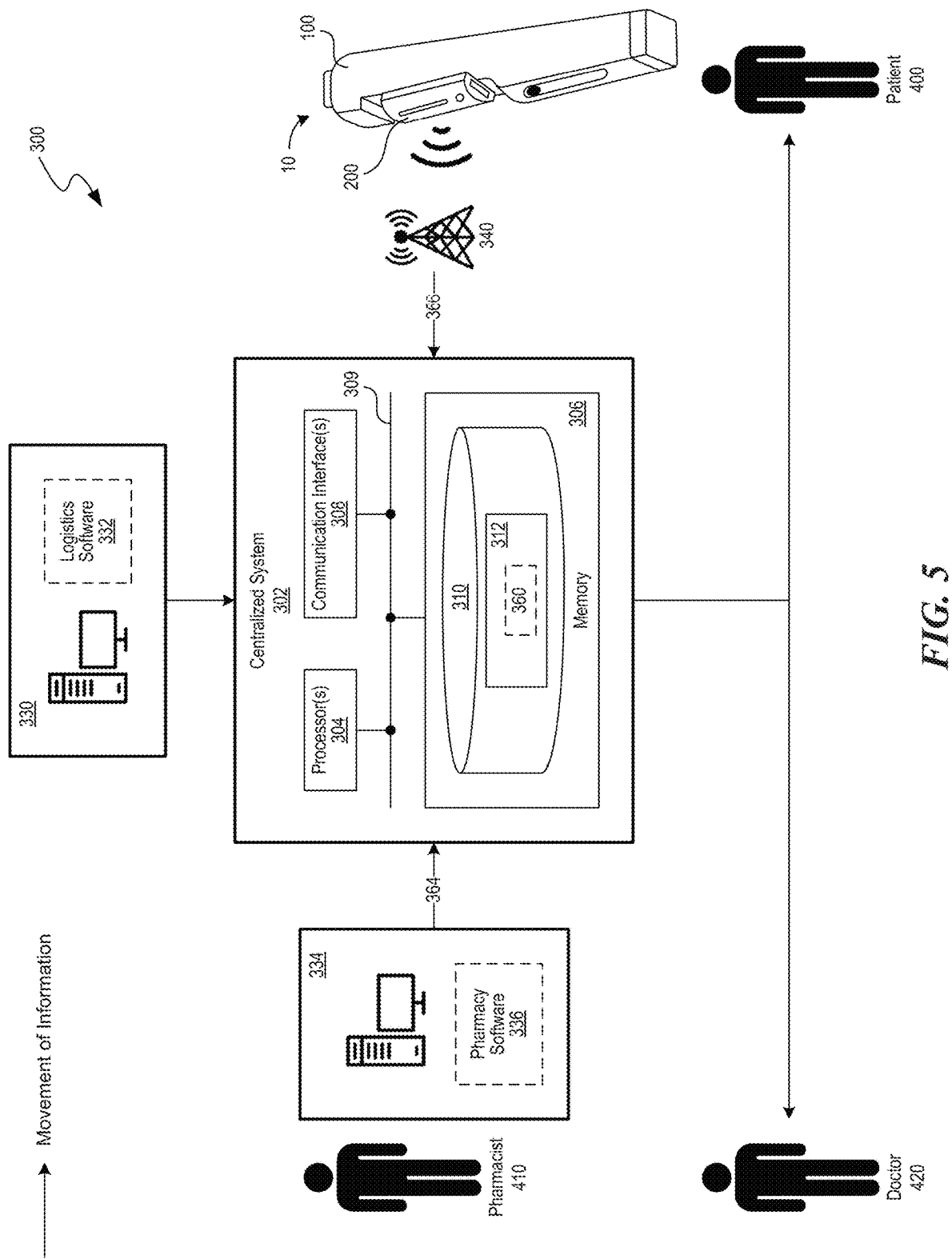
FIG. 5 depicts a flow of information within an example system architecture for tracking a distribution, dispensation, and use of the disposable drug delivery devices, in accordance with an embodiment of the present technology.

Example Communication and Tracking System, Associated Devices, and Operation and FIG. 5 illustrates a flow of information within an example system architecture 300 for tracking distribution, dispensation, and use of the disposable drug delivery devices 100, in accordance with an embodiment of the present technology. As illustrated in FIG. 5, all the information flows through a centralized system 302, including information related to the distribution and dispensation of the drug delivery device 100, an identity of the medicament inside the drug delivery device 100, as well as an identity of a patient 400 associated with the drug delivery device 100.

In some embodiments, the centralized system 302 comprises a computerized system remote from the semi-reusable medicament assembly 10 and configured to communicate with the semi-reusable medicament assembly 10 (e.g., receive and send data from/to the assembly 10). In general, the centralized system 302 may include a processing system comprising processor(s) 304 and a memory 306 operatively coupled with the processor(s) 304 (e.g., coupled together with the processor(s) via a bus 309 and/or other mechanism). The processor(s) 304 may comprise one or more central processing units (CPUs), dedicated processors (e.g., ASIC(s)), or general purpose processors (e.g., DSPs) configured to execute computer-readable program code or instructions. The memory 306 may be non-transitory computer-readable medium or media, and may be volatile or non-volatile type of data storage.

The memory 306 may store program logic including program instructions (e.g., machine language instructions and/or other suitable (e.g., higher-level) programming instructions) executable by the processor(s) to carry out various functions of the centralized system 302 as described herein. Additionally, the memory 306 may store any other data, such as data used by the processor(s) 304 in the execution of the program instructions. Any additional data may also be held in other data storage location(s) separate from the memory 306. Further, components of the centralized system 302 may be co-located or distributed physically and/or logically across a number of different entities, such as across one or more servers (e.g., physical and/or virtual servers) and one or more data storage devices. The centralized system 302 may further include a number of interfaces, examples of which include input/output (I/O) interfaces, user interface(s), and communication/network interface(s). The centralized system 302 may include other components as well.

In particular, in some embodiments, the centralized system 302 includes communication interface(s) 308 for communicating with the semi-reusable medicament assembly 10 and other entities, as shown by way of example in FIG. 5. In this regard, the semi-reusable medicament assembly 10 may communicate with the centralized system 302 via a wireless network 340. In some embodiments, the wireless network 340 comprises a cellular network, and the semi-reusable medicament assembly 10 may be configured to establish a wireless connection with a cell tower/base station of a radio access network of the cellular network. Although not shown, the centralized system 302 may be coupled with the wireless network 340 using any suitable wireless/wired communication network(s) and/or link(s). For example, cellular networks typically provide connectivity to other networks, including the PSTN and the Internet, via their core networks.

In certain embodiments, the centralized system 302 may comprise a cloud-based system, as generally understood in the art of cloud computing, that may be accessible via the Internet. As such, the program logic and other components of the centralized system 302, as described above, may reside on cloud server(s) and associated data storage device(s). An example of a suitable cloud computing environment for implementing the centralized system 302 is a web-based cloud service, such as Amazon Web Services™ available from Amazon, Inc. As such, data communications between the semi-reusable medicament assembly 10 and the centralized system 302 may be carried via the Internet and the wireless network 340 in accordance with any suitable communication protocols. However, in other embodiments, the centralized system 302 may be configured in other way(s), one example of which includes a private LAN.

As noted above, in some embodiments, the wireless network 340 comprises a cellular network. In other embodiments, the wireless network 340 may comprise another type of wireless network, preferably at least one wireless network that provides a wireless coverage over a relatively long range. This may facilitate mobility of the semi-reusable medicament assembly 10 and allow the assembly 10 to establish a wireless connection with the wireless network 340 for communications with the centralized system 302 from various locations to track the disposable drug delivery device 100. In addition, as will be described later, providing wireless service via a cellular network may facilitate selectively activating and de-activating wireless connectivity of the reusable electronic module 200.

As shown in FIG. 5, in some embodiments, the centralized system 302 further includes a central database 310 containing a medicament assembly record 312. In one embodiment, the central database 310 may be held in the memory 306, as shown in FIG. 5. In another embodiment, the central database 310 may be held in one or more data storages separate from the memory 306 and accessible by the centralized system 302.

In illustrative embodiments, the centralized system 302 is configured to receive information related to the semi-reusable medicament assembly 10 from one or more information sources. Further, the centralized system 302 is configured to store the information related to the semi-reusable medicament assembly 10. In particular, in some embodiments, the centralized system 302 may collect various information related to the semi-reusable medicament assembly 10 from a number of information sources (e.g., one or more distinct information sources), and centrally manage and store that information in a data repository, such the central database 310. As will be described in more detail, in some embodiments, the information source(s) may include any of (i) a point of production of the semi-reusable medicament assembly, (ii) a point of distribution of the semi-reusable medicament assembly, (iii) a point of dispensation of the semi reusable medicament assembly, and (iv) the reusable electronic module 200 of the semi-reusable medicament assembly 10.

In an example operation, the information related to the semi-reusable medicament assembly 10 includes information identifying the semi-reusable medicament assembly 10. The centralized system 302 is configured to create (or generate) the medicament assembly record 312 based on the information identifying the semi-reusable medicament assembly 10. Such identifying information may be collected from one or more peripheral systems at the point of production, during distribution, or at the point of dispensation. Various other information regarding the semi-reusable medicament assembly 10 may be then linked to, or associated with, the medicament assembly record 312, such as by storing such related information in the medicament assembly record 312. To illustrate, the medicament assembly record 312 may contain medicament information 360 related to an identity of the semi-reusable medicament assembly 10.

Note that although FIG. 5 illustrates one medicament assembly record 312 for the semi-reusable medicament assembly 10, it will be appreciated that the central database 310 may be configured to store a plurality medicament assembly records, each medicament assembly record being created for a respective semi-reusable medicament assembly. As such, a plurality of disposable drug delivery devices may be tracked via the centralized system 302.

Referring back to FIG. 5, the centralized system 302 may be in communication with one or more peripheral systems including, for example a logistics system 330 and a pharmacy system 334. The centralized system 302 may be interconnected with the peripheral systems via any suitable landline and/or wireless networks/communication links (e.g., a wireless/landline LAN, a wide area network (WAN), etc.). In general, each of the peripheral systems may comprise at least one processor and a memory, where the memory includes instructions, such as in the form of suitable software, which the processor can execute. By way of example, as illustrated in FIG. 5, the logistics system 330 includes a logistics software/program logic 332 and the pharmacy system 334 includes a pharmacy software/program logic 336. Each peripheral system may also include other elements, including, e.g., database(s) for storage of various data/information, such as information to be communicated to the centralized system 302

In certain embodiments, logistics information 362 related to the semi-reusable medicament assembly 10 is collected by the centralized system 302 from the logistics system 330 via the software 332 and stored in the medicament assembly record 312. In general, as will be described later, the logistics system 330 may be deployed at a point of distribution of the semi-reusable medicament assembly 10. In addition, prescription information 364 related to semi-reusable the medicament assembly 10 is collected from the pharmacy system 334 via the pharmacy software 336 and stored in the medicament assembly 312. In this regard, when the semi-reusable medicament assembly 10 is dispensed by a pharmacist 410, the semi-reusable medicament assembly 10 is associated with the patient 400 within the centralized system 302.

As noted above, one of the information sources from which information related to the semi-reusable medicament assembly 10 may be collected at the centralized system 302 is the reusable electronic module 200 included in the semi-reusable medicament assembly 10. More specifically, as described in connection with FIGS. 2 and 4, the reusable electronic module is configured to collect information regarding a use of the disposable drug delivery device, particularly drug delivery performance information. The information regarding the use of the disposable drug delivery device 100 may be provided by the reusable electronic module 200 to the centralized system 302.

To illustrate, when the patient 400 uses the disposable drug delivery device 100 to administer a dose of medicament, the reusable electronic module 200 records and sends information regarding drug delivery performance 366. The drug delivery performance information 366 is sent by the reusable electronic module 200 through the wireless network 340. As noted above, in certain embodiments, the wireless network 340 comprises a cellular network. The drug delivery performance information 366 received from the reusable electronic module 200 is stored within the medicament assembly record 312.

In certain embodiments, the centralized system 302 distributes the medicament information 360 and the drug delivery performance information 366 to the patient 400 and a care provider 420. Such information may be important for managing treatment regimens and remotely monitoring and supporting the patient 400. In further embodiments, the information contained within the medicament assembly record 312 is also distributed to a pharmacist 410 for monitoring and supporting the patient 400. In some embodiments, information flows bidirectionally between the centralized system 302 and the information sources, including, e.g., the logistics system 332, the pharmacy system 334, and the reusable electronic module 200.

Figure 6:
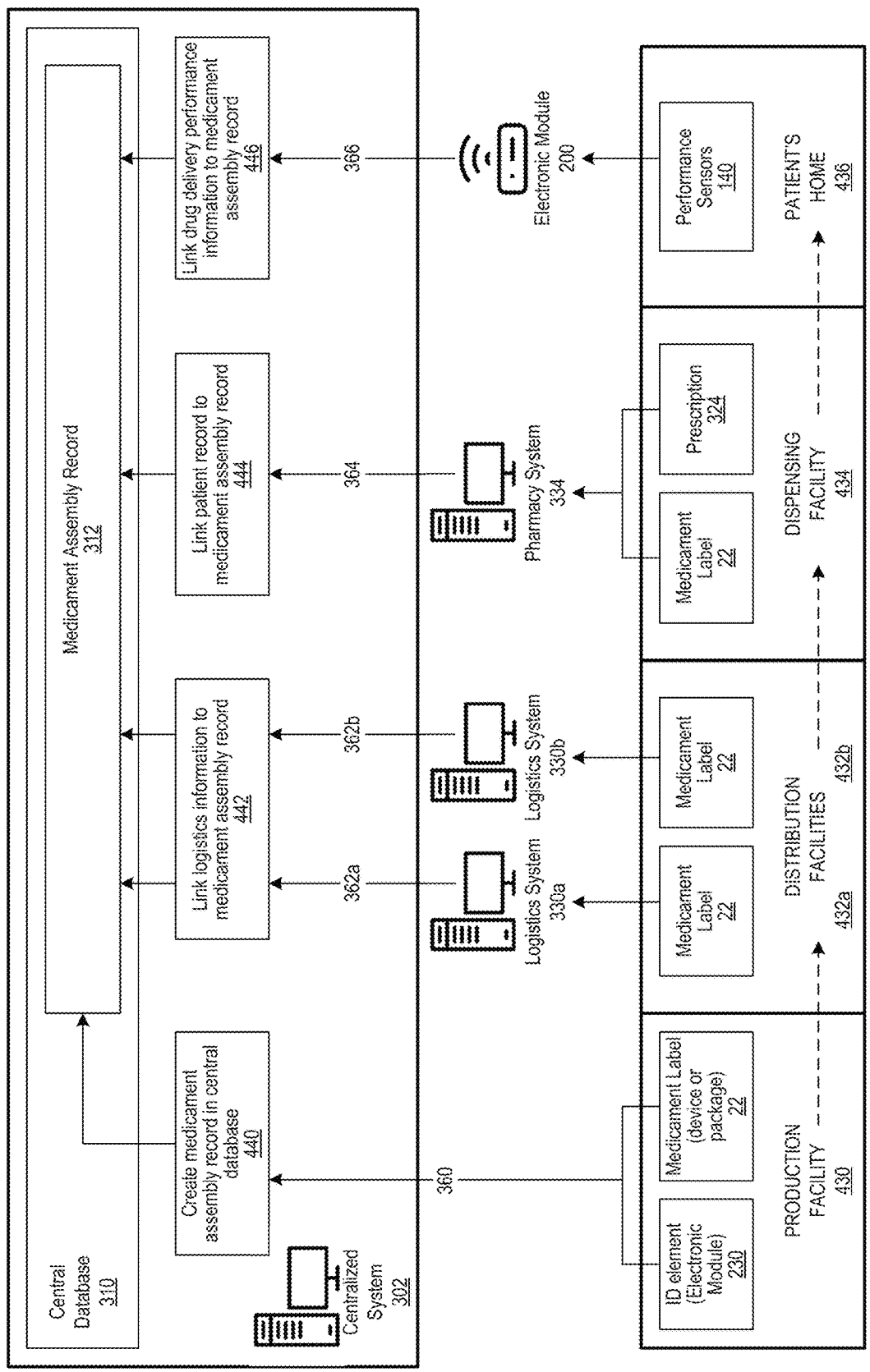
FIG. 6 is a block diagram illustrating an example of a workflow and system architecture associated with a process for tracking drug disposable delivery devices, including tracking a distribution, dispensation, and use of the disposable drug delivery devices, in accordance with an embodiment of the present technology.

FIG. 6 is a block diagram illustrating an example of a workflow and system architecture associated with a process for tracking drug disposable delivery devices, including tracking a distribution, dispensation, and use of the disposable drug delivery devices, in accordance with an embodiment of the present technology. In some embodiments, the process starts at a point of production, such as a production facility 430, where information identifying the semi-reusable medicament assembly 10 is communicated to the centralized system 302. Namely, an information from the electronic module ID element 230 indicative of an identity of the reusable electronic module 200 and an information from the medicament label 22 indicative of an identity of the medicament 112 in the disposable drug delivery device 100 are uploaded to the centralized system 302. This results in the creation of a medicament assembly record 312 within the central database 312 (block 440).

In certain embodiments, the centralized system 302 is directly connected to a production and assembly machinery responsible for scanning products coming off the assembly line. In other embodiments, there is a production system that connects to the machinery and sends data to the centralized system 312. The process continues through distribution, where the semi-reusable medicament assembly 10 is tracked by logistics system 330a, 330b deployed at distribution facilities 432a, 432b, respectively. In certain embodiments, the semi-reusable medicament assembly 10 is tracked by executing the logistics software 332 when the ID element 230 of the reusable electronic module 200 is scanned. In other embodiments, the semi-reusable medicament assembly 10 is tracked by scanning the medicament label 22. Logistics information 362a, 362b collected at each distribution facility 432a, 432b is sent to the centralized system 302 and linked to the appropriate medicament assembly record 312 associated with the semi-reusable medicament assembly 10 (block 442).

Referring back to FIG. 6, the process of tracking the disposable drug delivery device 100 continues at a point of dispensation of the semi-reusable medicament assembly 10, such as a dispensing facility 434. In the dispensing facility 434, the semi-reusable medicament assembly 10 is tracked by executing the pharmacy software 336. In some embodiments, the medicament assembly 10 is tracked by executing the pharmacy software 336 when the electronic module ID element 230 of the reusable electronic module 200 is scanned. In other embodiments, the medicament assembly 10 is tracked by scanning the medicament label 22.

During the dispensing event, the medicament assembly 10 is associated with a prescription information 364 within the centralized system 302. The prescription information 364 includes an identity of the patient 322 receiving a prescription for the disposable drug delivery device 100. The prescription information 364 also includes a medicament identity 318 and the medicament information 360. In certain embodiments, the pharmacy software 336 causes the pharmacy system 334 to send the prescription information 364, including the medicament identity 318 and the patient identity 322, to the centralized system 302. The centralized system 302 links, or associates, the medicament assembly record 312 with a patient record 320 within the central database 310 based on the patient identity 322 in the prescription information 364 (block 444). In this regard, the centralized system 302 may, for example, store the medicament assembly record 312 within the patient record 320. However, in other embodiments, the association between the medicament assembly record 312 and the patient record 320 may be established in other way(s). If there is no existing patient record 310 for the patient identity 322 (e.g., no prior prescription exists on record for a given patient), the centralized system 302 creates a new patient record 310a that is linked to the medicament assembly record 312.

In various embodiments, the prescription information may be broken up into two different types of information: prescription information and dispensation information. For example, the prescription information may include information about a medicament being prescribed to a patient. In such an embodiment, this information may be sent and updated to records when the medicament is prescribed and before it is actually dispensed. Accordingly, the prescription information in this embodiment may include information such as the medicament, dosing information, information about the patient, information about the pharmacy or other dispensing entity that is to dispense the medicament, time/day that the medicament is prescribed, etc. The dispensation information, then, can be related strictly to when, how, etc. the medicament (including any electronic modules and drug delivery devices associated therewith) are actually dispensed to the patient. Such information may include how the medicament is dispensed (e.g., through the mail, in person at a pharmacy), how the medicament was paid for, where the medicament was dispensed, time/day the medicament was dispensed, how much medicament was actually dispensed, identification information of the particular medicaments dispensed (including any information relating to a medicament package the medicament is stored in), etc. Accordingly, prescription information and dispensation information can include different types of information and can be updated in records at different times based on the times of prescription and actual dispensation of medicament. In some embodiments, the prescription and dispensation information are sent to a server to update a record at the same time. For example, in some embodiments, the prescription information is sent to the server to update a record at or near the dispensation event, such that there is not an update to a record or system when a drug is prescribed, but only when it is dispensed.

In certain embodiments, the dispensing facility 434 is a specialty pharmacy that mails the medicament to a patient's home 436. The process of tracking the disposable drug delivery device 100 continues while it is used by the patient 400 to administer a dose. In some embodiments, the reusable electronic module 200 records the drug delivery performance information 366 from the one or more performance sensors 140 during the dosing event. The drug delivery performance information 366 is then wirelessly sent to the centralized system 302 by the reusable electronic module 200. Based on an electronic module identity 316, the centralized system 302 links the drug delivery performance information 366 to the appropriate medicament assembly record 312 (block 446).

In some embodiments, the disposable drug delivery device 100 contains enough medicament 112 for multiple doses. In such embodiments, the drug delivery performance information 366 is recorded and sent by the electronic module 200 for each dosing event. In such embodiments, all of the drug delivery performance information 366 generated by the medicament assembly 10 during use is stored within the medicament assembly record 312.

Figure 7:
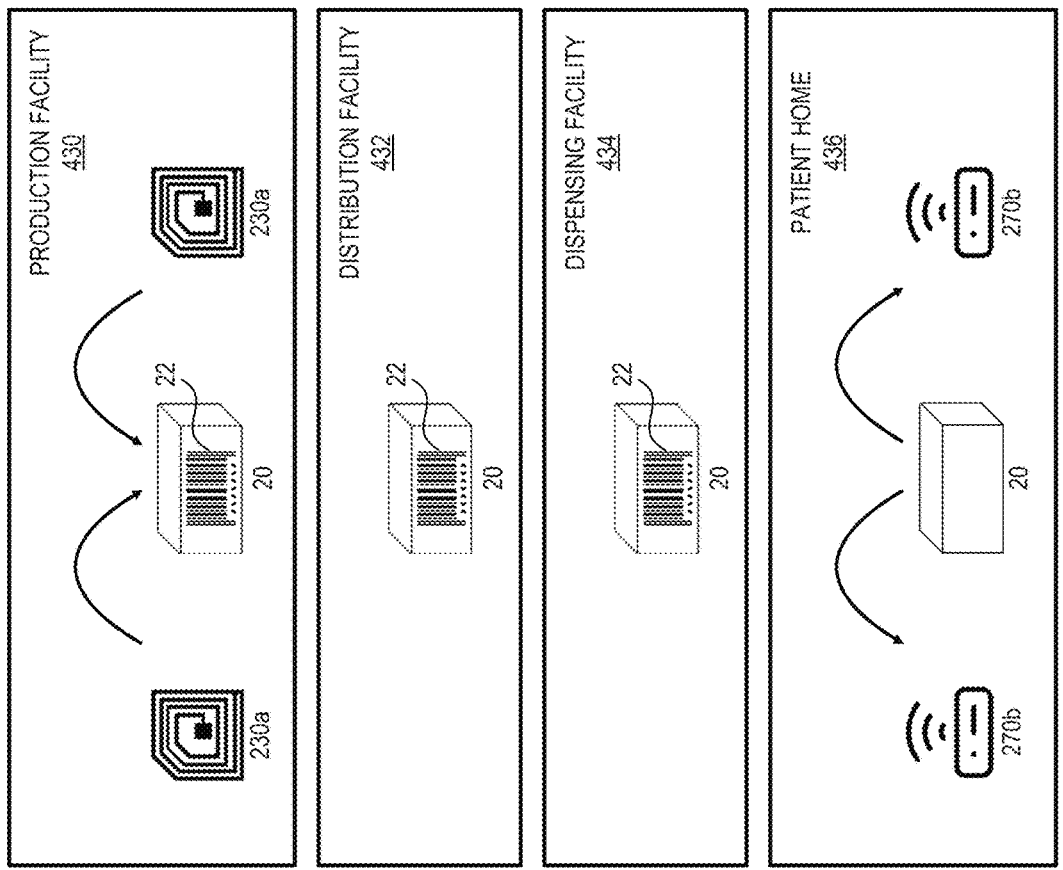
FIG. 7 is a block diagram illustrating data collection points for tracking a distribution, dispensation, and use of disposable drug delivery devices, in accordance with an embodiment of the present technology.
Figure 7:
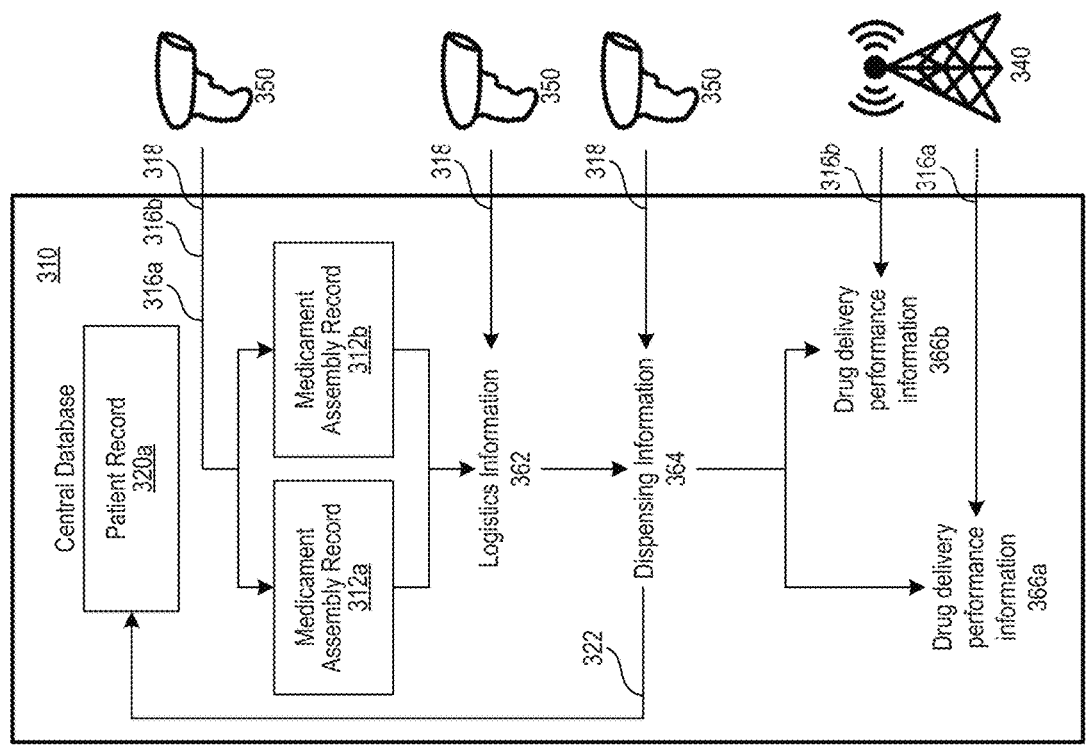

FIG. 7 is a block diagram illustrating data collection points for tracking distribution, dispensation, and use of disposable drug delivery devices, in accordance with an embodiment of the present technology. In some embodiments, information is collected by a scanner 350 during production, distribution, and dispensing. The first point of data collection occurs in the production facility 430, where identifying information related to the medicament assembly 10, including the electronic module identity 316 and the medicament identity 318, is collected. The electronic module identity 316 can be collected by scanning the electronic module ID element 230. In some embodiments, the electronic module ID element 230 is an RFID tag embedded in the electronic module 200. The medicament identity 318 can be collected by scanning the medicament label 22. In certain embodiments, the medicament label 22 is present on the disposable drug delivery device. In other embodiments, the medicament label 22 is present on a medicament package 20, which can contain one or more semi-reusable medicament assemblies 10.

In such embodiments, all of the medicament assemblies in the medicament package 20 share the same medicament identity 318 but have unique electronic module identities 316a, 316b. When the medicament identity 318 is linked, or associated with, to the electronic module identity 316, a medicament assembly record 312 is created. In some embodiments, the medicament identity 318 is linked to the electronic module identity 316 through synchronized scanning of the medicament label 22 and the electronic module ID element 230, respectively. In further embodiments, multiple medicament assembly records 312a, 312b are created upon synchronized scanning of the medicament label 22 on the medicament package 20 and the electronic module ID elements 230a, 230b inside the medicament package 20. In such embodiments, the electronic module identities 316a, 316b result in the creation of unique medicament assembly records 312a, 312b, both of which are linked to the same medicament identity 318.

Once the medicament assembly record 312 has been created, the medicament assembly 10 can be tracked through distribution and dispensing using the medicament identity 318 or the electronic module identity 316. As described above, in various embodiments the information is collected by the scanner 350 during distribution and dispensing of the medicament assembly 10. In certain embodiments, the medicament label 22 on the package 20 is scanned at the distribution facility 432. The scan results in the logistics information 362 being linked to the medicament identity 318 indicated by the label 22. The linkage of the logistics information 362 to the medicament identity 318 creates a transitive link between the logistics information 362 and the one or more medicament assembly records 312a, 312b that are associated with the medicament identity 318.

The logistics information 362 may include details related to the distribution facility 432, as well as details related to the courier service used to pick up and drop off the medicament package 20. In certain embodiments, the medicament label 22 is scanned again at the dispensing facility 434, which results in the prescription information 364 being linked to the medicament identity 318 indicated by the label 22. The linkage of the prescription information 364 to the medicament identity 318 creates a transitive link between the prescription information 364 and the one or more medicament assembly records 312a, 312b that are associated with the medicament identity 318. The prescription information 364 includes the identity of the patient 400 prescribed the medicament assembly 10.

In some embodiments, the patient 400 is prescribed the medicament package 20 containing multiple medicament assemblies 10. In various embodiments, the patient identity 322 in the prescription information 364 transitively links the medicament assembly records 312a, 312b that are associated with the medicament identity 318 to the patient record 320 in the central database 310. In other embodiments, the centralized system 302 creates a new patient record 320a when no match exists between the patient identity 322 and the existing patient record 320.

In reference to FIG. 7, the final point of data collection is when the medicament assembly 10 is used to deliver the medicament 112 contained in the drug delivery device 100. In various embodiments, the medicament assembly 10 is used by the patient 400 at the home 436. In some embodiments, the medicament assembly 10 is taken out of the medicament package 20 when the patient 400 is ready to administer a dose. In further embodiments, each medicament assembly 10 is for single use, containing a single dose of the medicament 112. In such embodiments, the electronic module 200 sends the drug delivery performance information 366 through the wireless network 340. The drug delivery performance information 366 is then transitively linked to the appropriate medicament assembly record 312 based on the identity 316 of the electronic module 200 that wirelessly sent it.

For example, a patient may be prescribed an injectable therapy that must be taken twice a month. That patient would receive a medicament package containing two first and second medicament assemblies with the same medicament identity 318. Each medicament assembly comprises a respective first and second disposable drug delivery device and a respective first and second electronic module operatively coupled to the disposable drug delivery device. When the patient uses the first semi-reusable medicament assembly, the first electronic module wirelessly sends first drug delivery performance information 366a using an RF transceiver 270a of the first electronic module. The centralized system 302 stores the first drug delivery performance information 366a in an appropriate medicament assembly record associated with the first semi-reusable medicament assembly, such as the medicament assembly record 312a based on the identity 316a of the electronic module that sent it. The same process occurs for the second semi-reusable medicament assembly, resulting in second drug delivery performance information 366b for the second monthly dosing event being stored in a different medicament assembly record associated with the second semi-reusable medicament assembly, such as the medicament assembly 312b. Both of the medicament assembly records 312a, 312b associated with the medicament identity 318 are linked to the patient record 320 for the patient dispensed the medicament package 20.

Figure 8A:
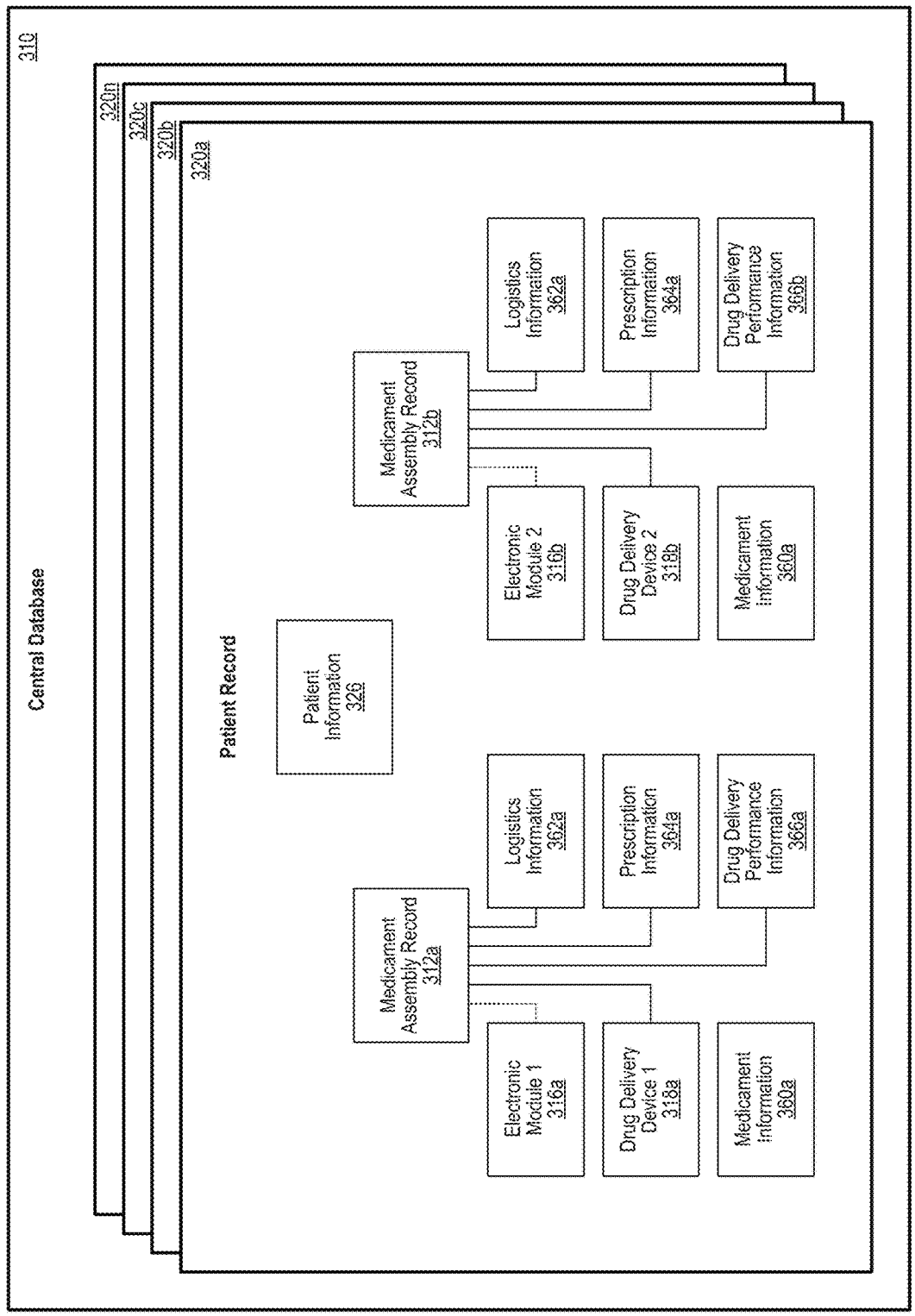
FIGS. 8A and 8B are block diagrams illustrating an organizational relationship of information within a central database of a centralized system, in accordance with an embodiment of the present technology.
Figure 8B:
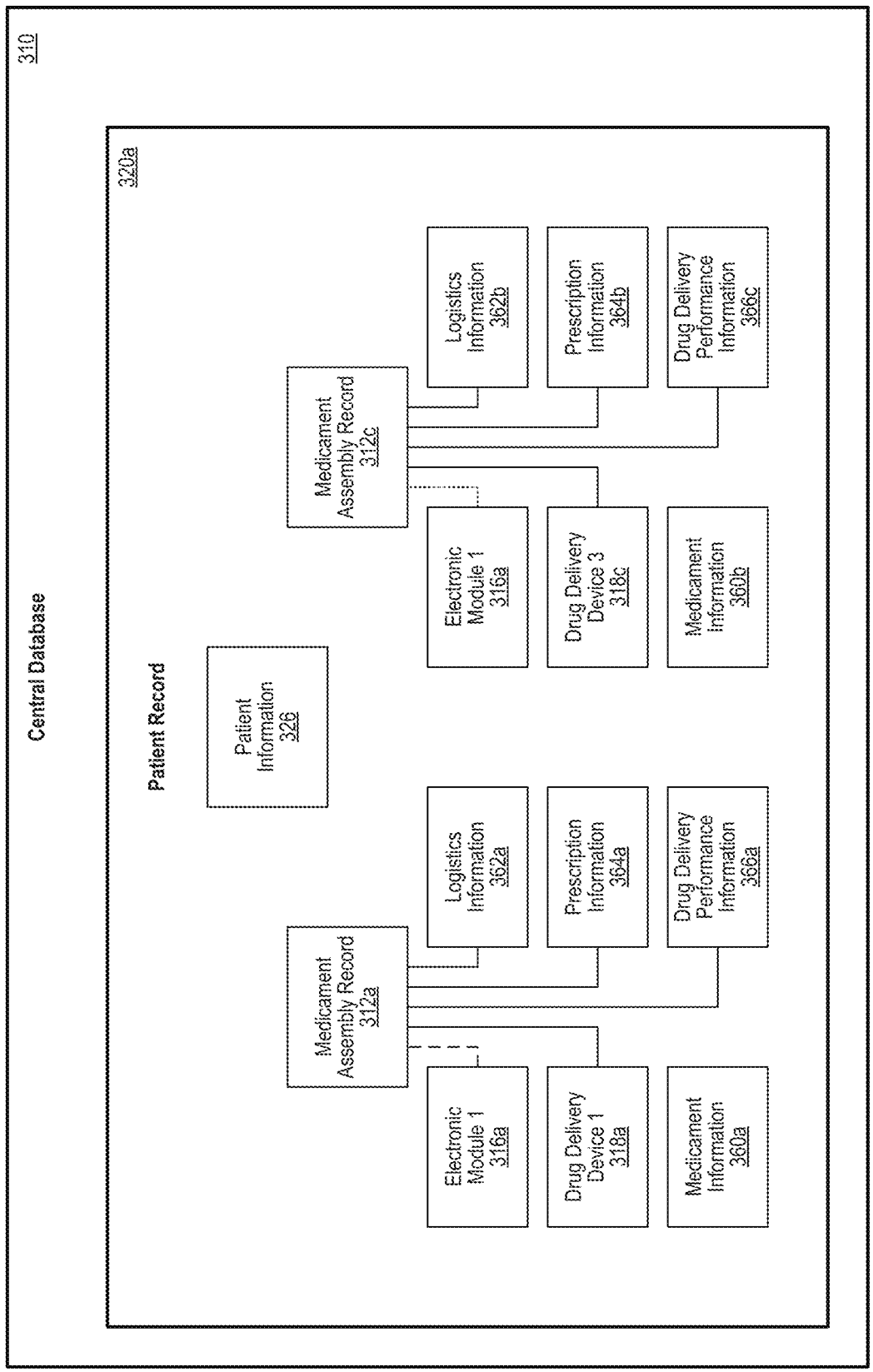

FIGS. 8A and 8B are block diagrams illustrating an organizational relationship of information within the central database 310 of the centralized system 302, in accordance with an embodiment of the present technology. FIG. 8A shows an example of the patient record 320a (see also FIG. 7) being stored within the central database 310 alongside other patient records 320b, 320c . . . 320n. The patient record 320a contains patient information 326 related to the patient 400 as well as multiple medicament assembly records 312a, 312b linked to the patient identity 322 at the point of dispensation. Patient information 326 can include the patient identity 322, as well as demographic, medical and treatment information related to the patient. In various embodiments, the first medicament assembly record 312a contains information related to a semi-reusable medicament assembly, including the electronic module identity 316a, medicament identity 318a and medicament information 360a. In certain embodiments, the medicament identity 318a is specific to a respective drug delivery device (denoted as "Drug Delivery Device 1") that an electronic module (denoted as "Electronic Module 1") with the identity 316A is operatively coupled to. In other embodiments, the medicament identity 318a is tied to a medicament package that may contain multiple drug delivery devices containing medicament having the identical medicament information 360a. The medicament information 360a can include national drug code, lot number, expiration date and dosage. In various embodiments, the medicament assembly record 312a contains logistics information 362a, prescription information 364a and the drug delivery performance information 366a.

As shown in FIG. 8A and described above in connection with FIG. 7, a medicament package that contains multiple semi-reusable medicament assemblies may result in the creation of multiple medicament assembly records 312a, 312b, respectively. The medicament assembly records 312a, 312b will both be linked to the same patient record 320a based on the patient identity 322 collected from the prescription information 364a at the point of dispensation. The medicament assembly records 312a, 312b for the multiple medicament assemblies distributed and dispensed in the same medicament package may have the same medicament information 360a, logistics information 362a, and prescription information 364a. However, they will have different electronic module identities 316a, 316b and different drug delivery performance information 366a, 366b based on different medicament assemblies used by the patient in distinct dosing events. In certain embodiments, they may also have different medicament identities 318a, 318b if tracked at the drug delivery device level. In other embodiments, however, they will have the same medicament identity 318a when tracked at the medicament package level.

FIG. 8B shows the same exemplary patient record 320a with a third medicament assembly record 312c included in the patient record 320a. The third medicament assembly record 312c is generated upon linking, to the new medicament identity 318c, the electronic module identity 316a of the electronic module (i.e., the Electronic Module 1) when that electronic module is recycled to and operatively coupled to a new disposable drug delivery device (denoted as "Drug Delivery Device 3"). The identity 316a of the recycled electronic module is linked within the central database 310 to multiple medicament assembly records 312a, 312c based on the distinct drug delivery devices (i.e., the Drug Delivery Device 1 and the Drug Delivery Device 3) that the recycled electronic module been operatively coupled to.

More specifically, the recycled electronic module is linked to multiple medicament identities 318a, 318c. The centralized system 302 maintains a registry of links between the electronic module identity 316a and the medicament identities 318a, 318c. In certain embodiments, the centralized system 302 only allows for one active link to exist for the electronic module identity 316a. In such embodiments, the link to the previous medicament assembly record 312a is archived. By maintaining a registry of active links, the centralized system 302 is able to link new logistics information 362b, prescription information 364b and drug delivery performance information 366c to the appropriate medicament assembly record 312c.

With reference to FIGS. 5-8B, the present technology allows for disposable drug delivery devices to be tracked through distribution at the device-level and the package-level, providing superior oversight and security for pharmaceutical supply chains. In addition, the present technology allows for remote tracking of a usage of disposable drug delivery devices without placing any additional burden on a patient. The patient can simply use a disposable drug delivery device to administer a medicament contained therein, while drug delivery performance information is passively recorded and sent for a storage in an appropriate patient record. This enables objective and real-time monitoring of medication adherence without any setup or syncing required by the patient.

Selected Embodiments of Exemplary Methods

Several suitable methods are disclosed herein and discussed further below; however, these methods are provided by way of example and one of ordinary skill in the art will appreciate that one or more other suitable methods may be possible as well. With respect to the embodiments illustrated in FIGS. 1A-8B, a semi-reusable medicament assembly as described herein can be used to deliver a parenteral medicament to a subject. Some methods include steps for producing and using the semi-reusable medicament assembly. Additional methods include steps for tracking a distribution, dispensation, and use of the semi-reusable medicament assembly.

Figures 9A, 9B:
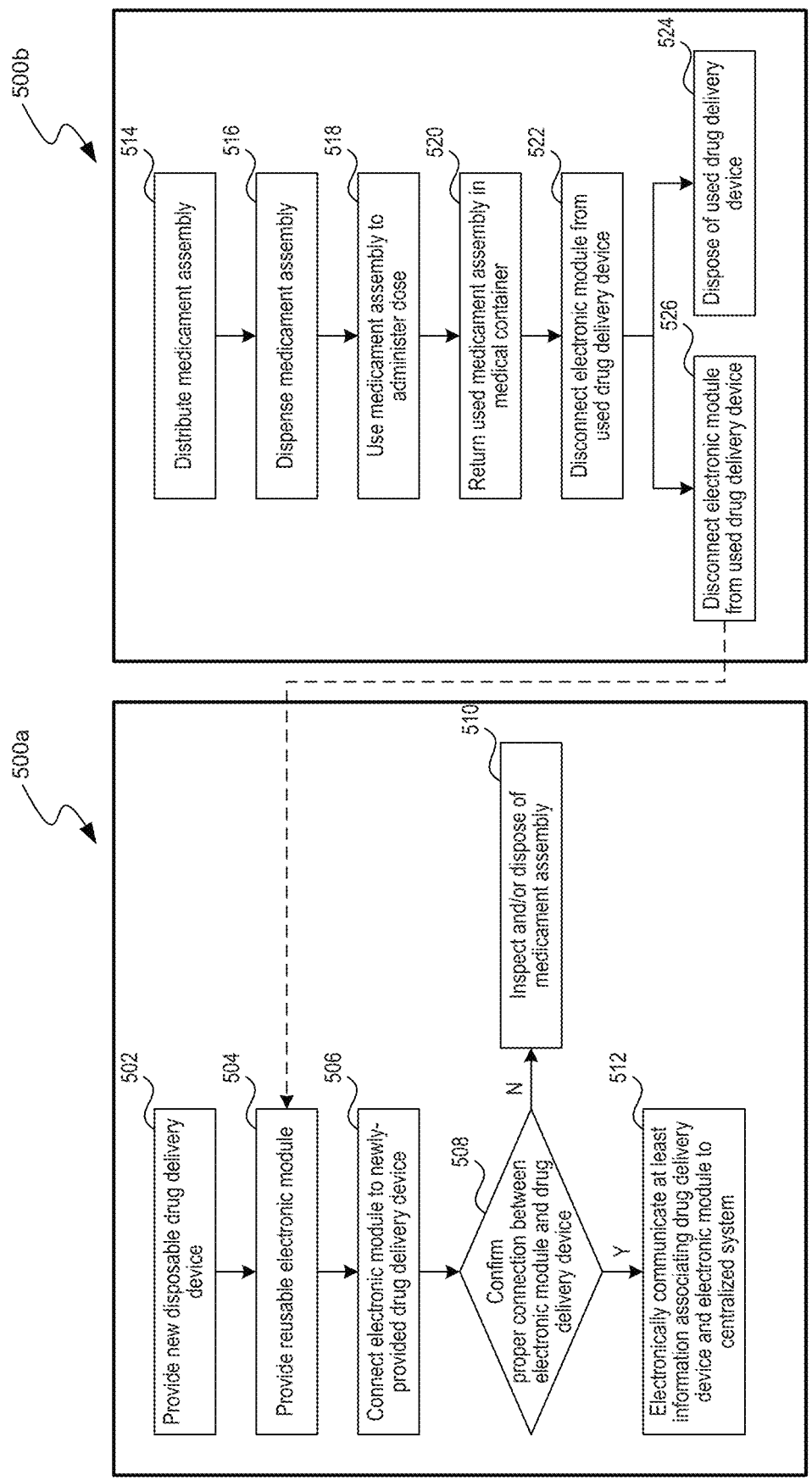
FIG. 9A is a flow diagram illustrating a method for producing a semi-reusable medicament assembly, in accordance with an embodiment of the present technology.
FIG. 9B is a flow diagram illustrating a method that may be carried out post-production of the semi-reusable medicament assembly, in accordance with an embodiment of the present technology.

FIG. 9A is a flow diagram illustrating a method 500A for producing a semi-reusable medicament assembly, in accordance with an embodiment of the present technology. The method can begin with providing a new disposable drug delivery device (block 502) containing a parenteral medicament. In some embodiments, the disposable drug delivery device may be assembled. In other embodiments, it may come pre-assembled. Further, the disposable drug delivery device may be an auto-injector for injectable therapies or an inhaler for respiratory medicaments.

The method 500A continues with providing a reusable electronic module (block 504) and operatively coupling the disposable drug delivery device with the reusable electronic module (block 506). The reusable electronic module may be a newly-assembled or it may be recycled from another previous semi-reusable medicament assembly. In some embodiments, the assembly may undergo quality testing such as to test for a proper connection between the disposable drug delivery device and the reusable electronic module (block 508). In some embodiments, a test for proper connection to the disposable drug delivery device may result in a generation of a signal by the reusable electronic module. Such signal confirms that the reusable electronic module is in mechanical and/or electrical engagement with the disposable drug delivery device. In some embodiments, the signal is an optical signal, such as in form of an LED turning on. In some embodiments, the signal is a wireless communication signal generated by the reusable electronic module. In some embodiments, if the proper connection cannot be confirmed, the medicament assembly may be disposed of and/or inspected (block 510).

The method 500A continues with electronically communicating at least an information associating the disposable drug delivery device with the reusable electronic module to a remote centralized system, such as the centralized system 302, configured to store that information (e.g., in a database) (block 512). As described above in connection with FIG. 6, information identifying the semi-reusable medicament assembly may be communicated to the remote centralized system from a production facility. In some embodiments, the identifying information may include an information read from an electronic module ID element indicative of an identity of the reusable electronic module and an information read from a medicament label indicative of an identity of the medicament contained in the disposable drug delivery device. Such information may be electronically communicated to the centralized system via suitable hardware/software deployed at the production facility.

FIG. 9B is a flow diagram illustrating a method 500B that may be carried out post-production of the semi-reusable medicament assembly of FIG. 9B, in accordance with an embodiment of the present technology. After production, the semi-reusable medicament assembly may be distributed and dispensed to a patient (blocks 514 and 516). The patient uses the semi-reusable medicament assembly to administer one or more doses, and then disposes of the semi-reusable medicament assembly in a medical container once the disposable drug delivery device is emptied of a medicament (blocks 518 and 520). In some embodiments, the medical container is a rigid sharps container. The patient then returns the used medicament assembly in the medical container back to an appropriate facility for recycling (block 520). In some embodiments, the recycling facility is the same as the production facility. The method 500B continues with a recycling of the reusable electronic module, starting with disconnecting the electronic module from the emptied drug delivery device (block 522). The used drug delivery device is then disposed of (block 524), while the electronic module undergoes processing for reuse. In some embodiments, such processing includes cleaning and sterilizing the used electronic module (block 526). In some embodiments, the reuse processing also includes testing functionality of the used electronic module. Once the electronic module has been fully processed, it may be connected to another new disposable drug delivery device (see blocks 504 and 506 of the method 500A).

Figure 10:
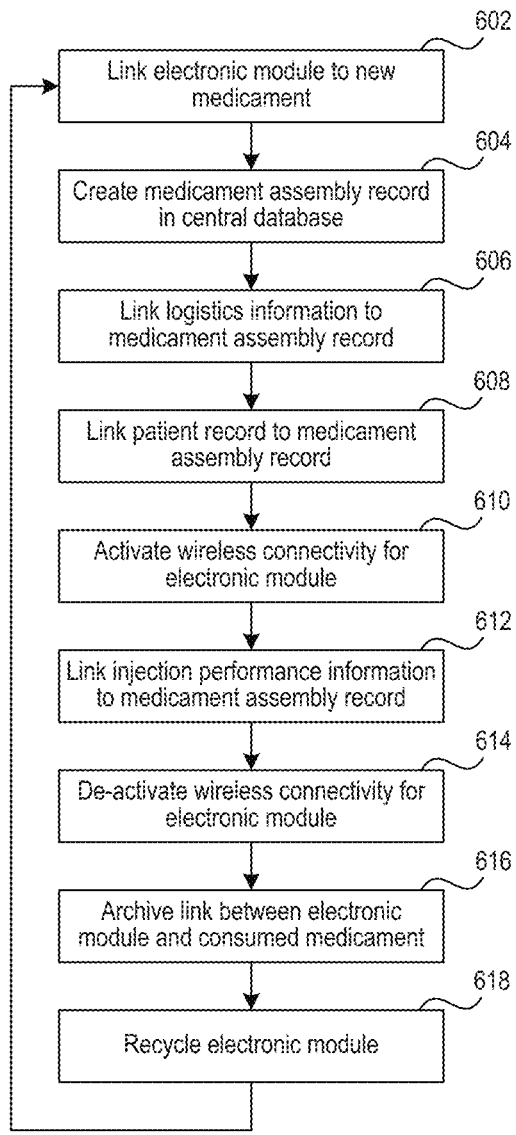
FIG. 10 is a flow diagram illustrating a method for a centralized system to track a distribution, dispensation, and use of a semi-reusable medicament assembly, in accordance with an embodiment of the present technology.

FIG. 10 is a flow diagram illustrating a method 600 for tracking a distribution, dispensation, and use of a semi-reusable medicament assembly, in accordance with an embodiment of the present technology. The method 600 begins with a creation of an active association or link at a remote centralized system between a reusable electronic module and an operatively-coupled drug delivery device containing a medicament (block 602). The creation of a new link results in a creation of a medicament assembly record in a central database of the centralized system (block 604). The medicament assembly record contains identities of the reusable electronic module and the medicament inside the disposable drug delivery device (as obtained, e.g., from a medicament label on the disposable drug delivery device or a package containing such device). In some embodiments, logistics information is linked to the medicament assembly record based on the identity of the reusable electronic module or the medicament (block 606). The medicament assembly record is then linked to a patient record based on a patient identity determined at a point of dispensation (block 608).

The method 600 continues with an activation of a wireless connectivity in the reusable electronic module following the linkage of the medicament assembly record to the patient record (block 610). In some embodiments, the wireless connectivity is activated by provisioning a cellular network access to a SIM card or another type of module that may be embedded in the reusable electronic module to identify/authenticate the reusable electronic module on a wireless network. In certain embodiments, the centralized system may be configured to send a provisioning request to a provisioning system of a wireless carrier selected, e.g., as a primary cellular service provider. The centralized system and the wireless carrier's system may be integrated or linked in various ways. Upon the receipt of the provisioning request, the wireless carrier can responsively enable the cellular network access for the SIM card of the reusable electronic module, thereby activating the wireless connectivity in the reusable electronic module. Once the wireless connectivity is activated, the reusable electronic module will be able to access the cellular network and send/receive data. The process of provisioning cellular network access by the wireless carrier may be carried out same way as is done with respect to other wireless devices for a given network access technology.

In various embodiments, the reusable electronic module uses the wireless connectivity to communicate injection performance information to the centralized system following a dosing event. The centralized system then links the injection performance information to the medicament assembly record based on the electronic module identity (block 612). In certain embodiments, the electronic module identity is communicated at the beginning of a data transmission event. In some embodiments, the electronic module identity is a SIM card serial number, which is linked to an electronic module ID element within the central database of the centralized system. Confirmation of the semi-reusable medicament assembly being used and emptied results in the centralized system de-activating wireless connectivity for the electronic module (block 614). In certain embodiments, the centralized system may be configured to send a de-activation request to the wireless carrier's system. Upon the receipt of the de-activation request, the wireless carrier can responsively disable the cellular network access for the SIM card of the reusable electronic module, thereby de-activating the wireless connectivity in the reusable electronic module. Once the wireless connectivity is de-activated, the reusable electronic module will no longer be able to access the cellular network and send/receive data. The process of de-activating cellular network access by the wireless carrier can be carried out same way as is done with respect to other wireless devices for a given network access technology.

In some embodiments, the disposable drug delivery device contains a single dose and confirmation of emptying is understood to occur upon wireless communication after the dosing event. In certain embodiments, the drug delivery device contains multiple doses and an amount of medicament remaining is calculated after each dosing event. After the wireless connectivity has been de-activated for the electronic module, the centralized system archives the link between the electronic module and the medicament assembly record for the emptied drug delivery device (block 616). In some embodiments, this archiving step occurs upon de-activation of the wireless connectivity. In other embodiments, the archiving step occurs after the electronic module is recycled (block 618). In such embodiments, the existing link is archived upon a creation of a new active link between the reusable electronic module and another new disposable drug delivery device.

In referring to FIGS. 9 and 10, the methods 500A-B and 600 can be combined for producing and tracking of a semi-reusable medicament assembly, in accordance with an embodiment of the present technology. In certain embodiments, any peripheral system(s) involved in the methods 500A-B are electronically connected to the centralized system responsible for carrying out method 600. In such embodiments, the centralized system of the method 600 is networked with peripheral system(s) involved in the production, distribution, and dispensation steps of the methods 500A-B. In such embodiments, information collected by the peripheral system(s) may be generated by scanning the electronic module ID element or the medicament label during production, distribution, and dispensation. In certain embodiments, as described above in connection with the method 600, the electronic module identity is linked to the medicament in the drug delivery device (block 602) upon confirmation of a proper connection between the electronic module and the drug delivery device (block 508). In such embodiments, these coordinated steps (blocks 508 and 602) lead to the creation of the medicament assembly record in the central database (block 604). The medicament assembly record then contains the electronic module identity and the medicament identity.

In such embodiments, information collected from the peripheral system(s) is linked to the appropriate medicament assembly record based on the scanned electronic module identity or medicament identity. For example, when a semi-reusable medicament assembly is scanned during distribution (block 514), the centralized system collects the logistics information from a peripheral system at a point of distribution and links it to the appropriate medicament assembly record (block 606). When the semi-reusable medicament assembly is scanned at the point of dispensation (block 516), the centralized system links the medicament assembly record to the appropriate patient record (block 608) based on the patient identity and prescription information collected from a peripheral system at the point of dispensation (e.g. a pharmacy system executing suitable software).

Figure 11:
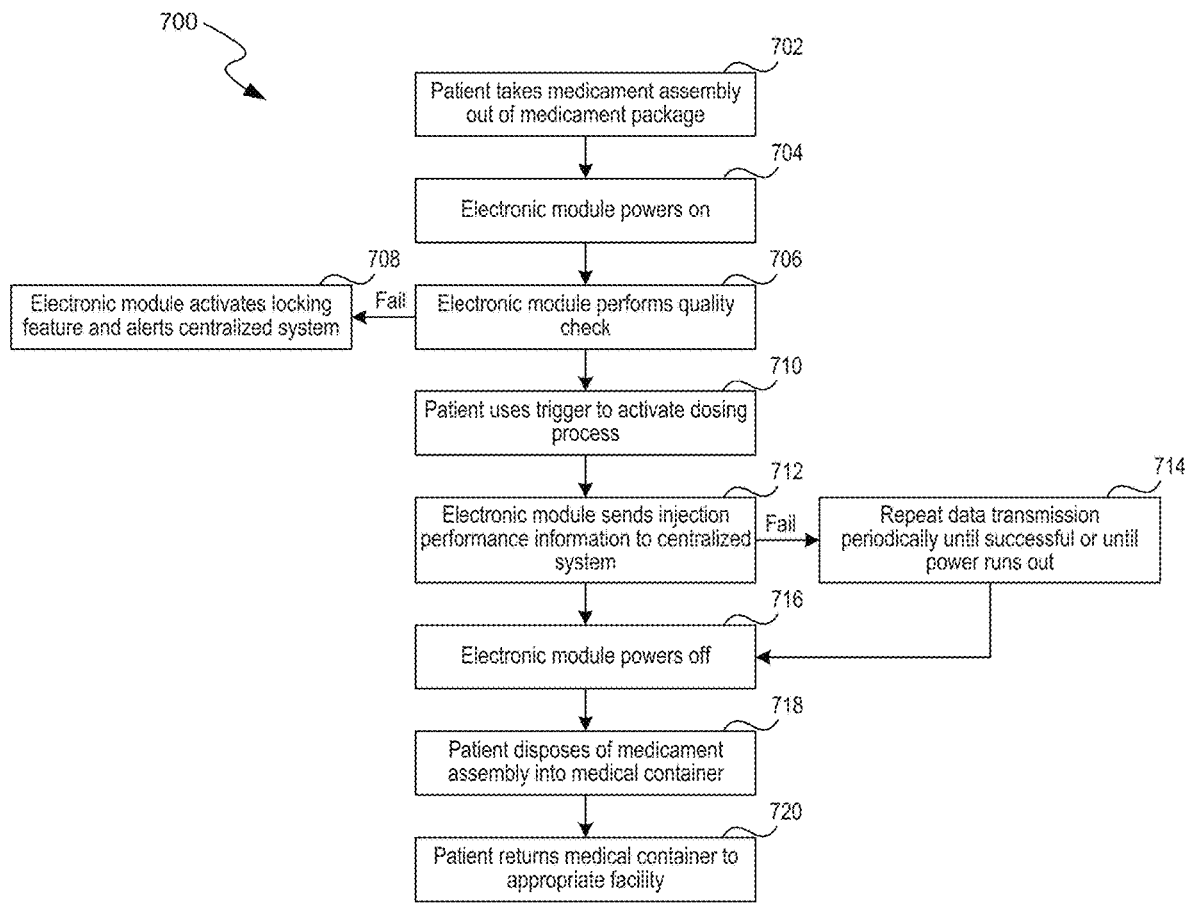
FIG. 11 is a flow diagram illustrating a method for using a semi-reusable medicament assembly, in accordance with an embodiment of the present technology.

FIG. 11 is a flow diagram illustrating a method 700 for using a semi-reusable medicament assembly, in accordance with an embodiment of the present technology. The method 700 can begin with a user taking the semi-reusable medicament assembly out of a medicament package (block 702). In some embodiments, the medicament package is a carton that contains multiple medicament assemblies. In some embodiments, the medicament assembly inside the package is kept refrigerated during storage. The method 700 can continue with a reusable electronic module powering on based on signals detected from the one or more activation sensors inside the electronic module (block 704). In some embodiments, the activation sensors include a light sensor, a temperature sensor and an accelerometer. In certain embodiments, the electronic module will perform a quality check once powered on (706). In such embodiments, the quality check can comprise checking for an expired, counterfeit or improperly stored dose. In some embodiments, the quality check involves wireless communication with the centralized system 302. In certain embodiments, a failed quality check leads to an activation of the electronic module's locking feature, which prevents administration of a medicament inside the disposable drug delivery device (block 708).

The method 700 continues with the patient using the medicament assembly to administer a dose of the medicament. In some embodiments, the dose is administered by the patient pressing on a trigger to initiate the dosing process (block 710). During the dosing process, the electronic module collects information from one or more performance sensors. In some embodiments, the performance sensors detect when the dosing event starts, when the dosing event finishes, and how much medicament was administered during the dosing event. Following completion of the dosing event, the electronic module sends information collected from the performance sensors to the centralized system (block 712). In some embodiments, the electronic module will repeatedly attempt to wirelessly transmit the performance information to the centralized system (block 714). Following the dosing event and the data transmission, the electronic module will automatically power off (block 716). Once the drug delivery device has been completely emptied of the medicament, the patient will dispose of the medicament assembly into a medical container (block 718).

In some embodiments, the drug delivery device is pre-filled with multiple doses of medicament, and the patient will put the medicament assembly back into storage until the next dosing event. In other embodiments, the drug delivery device contains a single dose and the patient disposes of the medicament assembly after a single use. The patient then returns the medical container to an appropriate facility (block 720). In some embodiments, the medical container is a sharps container. In some embodiments, the medical container can hold multiple used medicament assemblies before being filled and returned to the appropriate facility. In some embodiments, the medical container can be shipped to the appropriate facility. In some embodiments, the appropriate facility is a facility where the medicament assembly was produced.

In referring to FIGS. 10 and 11, the methods 600 and 700 can be combined for tracking a use of a semi-reusable medicament assembly, in accordance with an embodiment of the present technology. Information wirelessly communicated between the electronic module and the centralized system is linked to the appropriate medicament assembly record based at least on the electronic module identity. In some embodiments, the electronic module will request information from the centralized system during the quality check (block 706). In such embodiments, the centralized system will send data from the appropriate medicament assembly record based on the identity of the electronic module requesting the information. The centralized system will also store information received from the electronic module in the appropriate medicament assembly record (block 612) based on the identity of the electronic module sending the information.

Additional Embodiments

Features of the semi-reusable medicament assembly components described above and illustrated in FIGS. 1A-4 can be modified to form additional embodiments configured in accordance with the present technology. Various embodiments of systems, methods, apparatuses, and computer readable media are also described in the embodiments below:

1. An embodiment for a communication and tracking system for disposable drug delivery devices, the system comprising:
   a semi-reusable medicament assembly, the semi-reusable medicament assembly comprising a disposable drug delivery device and a reusable electronic module operatively coupled with the disposable drug delivery device; and
   a centralized system remote from the semi-reusable medicament assembly, the centralized system including at least one processor, wherein the centralized system is configured to receive, from one or more information sources, and store information related to the semi-reusable medicament assembly.
2. The system of embodiment 1, wherein the semi-reusable medicament assembly is configured to communicate with the centralized system via at least one wireless network.
3. The system of embodiment 2, wherein the at least one wireless network includes a cellular network.
4. The system of embodiment 1 or embodiment 2, wherein:
   the centralized system includes a central database, and
   the information received from the one or more information sources is stored in the central database.
5. The system of embodiment 1, wherein the one or more information sources include at least one of (i) a point of production of the semi-reusable medicament assembly, (ii) a point of distribution of the semi-reusable medicament assembly, (iii) a point of dispensation of the semi-reusable medicament assembly, and (iv) the reusable electronic module.
6. The system of embodiment 4, wherein the information related to the semi-reusable medicament assembly includes information identifying the semi-reusable medicament assembly.
7. The system of embodiment 6, wherein the centralized system is configured to receive the information identifying the semi-reusable medicament assembly from a point of production of the semi-reusable medicament assembly.
8. The system of embodiment 6, wherein the centralized system is configured to create a medicament assembly record based on the information identifying the semi-reusable medicament assembly.
9. The system of embodiment 8, wherein:
the information related to the semi-reusable medicament assembly further includes at least one of medicament information, logistics information, and drug delivery performance information, and
the centralized system is configured to store the at least one of medicament information, logistics information, and drug delivery performance information within the medicament assembly record.
10. The system of embodiment 8, wherein:
the semi-reusable medicament assembly is one of a plurality of semi-reusable medicament assemblies in a medicament package,
each semi-reusable medicament assembly in the medicament package has a unique electronic module identity, and
the centralized system is configured to create an individual medicament assembly record for each of the plurality of semi-reusable medicament assemblies in the medicament package.
11. The system of embodiment 10, wherein:
the semi-reusable medicament assembly includes a medicament, and
a medicament identity is the same for each semi-reusable medicament assembly in the medicament package.
12. The system of embodiment 8, wherein:
the disposable drug delivery device includes a medicament,
the information identifying the semi-reusable medicament assembly includes an electronic module identity and a medicament identity, and
the centralized system is configured to create the medicament assembly record on the basis of the electronic module identity and the medicament identity.
13. The system of embodiment 8, wherein:
the medicament assembly record is stored in the central database.
14. The system of embodiment 8, wherein the one or more information sources include a point of dispensation of the semi-reusable medicament assembly.
15. The system of embodiment 14, wherein the centralized system is configured to receive, from the point of dispensation, information identifying a patient associated with the semi-reusable medicament assembly when the semi-reusable medicament assembly is dispensed.
16. The system of embodiment 15, wherein the centralized system is configured to associate the medicament assembly record with a patient identity.
17. The system of embodiment 16, wherein the centralized system is configured to store a patient record containing the patient identity, and is further configured to link the medicament assembly record to the patient record based at least on the patient identity.

18. The system of embodiment 17, wherein the centralized system is configured to store the medicament assembly record within the patient record.

19. The system of embodiment 16, wherein:
the reusable electronic module has a wireless connectivity capability to wirelessly communicate with the centralized system, and
the reusable electronic module is configured such that a wireless connectivity is activated when the medicament assembly record is associated with the patient identity.

20. The system of embodiment 19, wherein the wireless connectivity enables the reusable electronic module to establish a wireless connection with a wireless network providing a relatively long range wireless coverage.

21. The system of embodiment 20, wherein the wireless network providing the relatively long range wireless coverage is a cellular network.

22. The system of embodiment 19, wherein the reusable electronic module is further configured such that the wireless connectivity is de-activated once the centralized system receives information that confirms an emptying of a medicament container in the semi-reusable medicament assembly.

23. The system of embodiment 14, wherein:
the reusable electronic module is configured to collect information regarding a use of the disposable drug delivery device, and
the one or more information sources further include the reusable electronic module.

24. The system of embodiment 23, wherein the information regarding the use of the disposable drug delivery device includes a drug delivery performance information of the disposable drug delivery device.

25. The system of embodiment 24, wherein the electronic module has one or more sensors and is configured to collect, from the one or more sensors, and store information related to the drug delivery performance during a dosing event.

26. The system of embodiment 24, wherein the drug delivery performance information includes a timestamp of a dosing event and an amount of medicament in the disposable drug delivery device that is administered.

27. The system of embodiment 24, wherein the electronic module is configured to wirelessly communicate at least a portion of the drug delivery performance information to the centralized system after a dosing event.

28. The system of embodiment 14, wherein the reusable electronic module is configured to perform a quality check upon a first power-on following a dispensation of the semi-reusable medicament assembly.

29. The system of embodiment 28, wherein information related to the quality check is stored in at least one of a memory of the electronic module and the medicament assembly record held in the central database of the centralized system.

30. The system of embodiment 28, wherein the reusable electronic module is configured to indicate a failed quality check when a medicament in the disposable drug delivery device is expired, recalled, or counterfeit.

31. The system embodiment 14, wherein:
the one or more information sources further include a point of distribution of the semi-reusable medicament assembly, and
the information related to the semi-reusable medicament assembly includes logistics information collected at the point of distribution of the semi-reusable medicament assembly.

32. The system of embodiment 1, wherein:
the disposable drug delivery device includes (a) a primary container filled with a medicament and (b) a drive mechanism for delivering the medicament into a user,
the reusable electronic module includes one or more engagement features configured to operatively couple to the disposable drug delivery device, and
the semi-reusable medicament assembly further comprises (a) a power source configured to provide power to the reusable electronic module and (b) one or more sensors configured to capture drug delivery performance information of the disposable drug delivery device.

33. The system of embodiment 32, wherein the reusable electronic module further comprises:
a processor programmed to control components and functions of the reusable electronic module,
a memory configured to store at least one of information collected from the one or more sensors and information communicated from the centralized system,
a machine-readable identification element, and
a wireless transceiver for communications with the centralized system over at least one wireless network.

34. The system of embodiment 33, wherein the at least one wireless network comprises a cellular network.

35. The system of embodiment 1, wherein the disposable drug delivery device is pre-filled with a medicament and configured to deliver the medicament into a body of a user.

36. The system of embodiment 1, wherein:
the centralized system is coupled to a first network,
the semi-reusable medicament assembly is coupled to a second wireless network, and
communications between the semi-reusable medicament assembly and the centralized system are carried over the first network and the second wireless network.

37. The system of embodiment 36, wherein the first network includes the Internet.

38. An embodiment for a semi-reusable medicament assembly, the assembly comprising:
a disposable drug delivery device comprising a primary container filled with a medicament and a drive mechanism for delivering the medicament into a user;
a reusable electronic module comprising one or more engagement features configured to operatively couple with at least one of (i) one or more mechanical features of the disposable drug delivery device and (ii) one or more electrical features of the disposable drug delivery device;
a trigger for the user to activate the drive mechanism;
a power source configured to provide power to the reusable electronic module; and
one or more sensors configured to capture drug delivery performance information of the disposable drug delivery device.

39. The assembly of embodiment 38, wherein the reusable electronic module further comprises:
a processor programmed to control components and functions of the reusable electronic module;
a memory configured to store at least one of information collected from the one or more sensors and information communicated from a remote centralized system, a machine-readable identification element; and
a wireless transceiver configured for communications with the remote centralized system over at least one wireless network.

40. The assembly of embodiment 39, wherein the at least one wireless network includes a cellular network.
41. The assembly of embodiment 39, wherein the reusable electronic module is configured to collect, from the one or more sensors, the drug delivery performance information during a dosing event, and to store the drug delivery performance information in the memory.
42. The assembly of embodiment 41, wherein the drug delivery performance information includes a timestamp of the dosing event and amount of the medicament administered.
43. The assembly of embodiment 41, wherein the reusable electronic module is configured to send, via the wireless transceiver, the drug delivery performance information to the remote centralized system.
44. An embodiment for a method for producing a semi-reusable medicament assembly, the method comprising:
providing a disposable drug delivery device;
providing a reusable electronic module;
operatively coupling the disposable drug delivery device with the reusable electronic module; and
electronically communicating at least information associating the disposable drug delivery device with the reusable electronic module to a remote centralized system, the remote centralized system including at least one processor and being configured to store the information.
45. The method of embodiment 44, wherein the reusable electronic module is a new electronic module or a recycled electronic module.
46. The method of embodiment 45, wherein the disposable drug delivery device contains a medicament, and the information associating the disposable drug delivery device with the reusable electronic module includes information identifying the electronic module and the medicament in the disposable drug delivery device.
47. The method of embodiment 46, further comprising:
creating, by the remote centralized system, a medicament assembly record for the semi-reusable medicament assembly on the basis of the information identifying the electronic module and the medicament in the disposable drug delivery device.
48. The method of embodiment 47, wherein:
the remote centralized system includes a central database, and
the medicament assembly record is stored in the central database.
49. The method of embodiment 47, wherein the reusable electronic module is configured such that the reusable electronic module can be decoupled from the disposable the drug delivery device.
50. The method of embodiment 49, wherein, once decoupled, the reusable electronic module is recycled and the disposable drug delivery device is disposed.
51. The method of embodiment 50, further comprising:
operatively coupling the recycled electronic module to a new disposable drug delivery device.
52. The method of embodiment 51, further comprising:
electronically communicating second information associating the new disposable drug delivery device with the recycled electronic module to the remote centralized system, and
linking, at the remote centralized system, an identity of the recycled electronic module to a second medicament inside the new disposable drug delivery device to create a new medicament assembly record.
53. The method of embodiment 50, wherein when the reusable electronic module is recycled, the module is separated from the disposable drug delivery device, cleaned, and tested for quality and functionality.
54. The method of embodiment 46, further comprising:
activating, by the remote centralized system, a link between the reusable electronic module and the medicament in the disposable drug delivery device.
55. The method of embodiment 46, wherein an electronic module identity is obtained from an identification element of the reusable electronic module.
56. The method of embodiment 46, wherein a medicament identity is read from at least one of a first medicament label on the disposable drug delivery device and a second medicament label on a medicament package containing the disposable drug delivery device.
57. An embodiment for a method for tracking disposable drug delivery devices, the method comprising:
receiving, from one or more information sources, at a centralized system remote from at least one semi-reusable medicament assembly, information related to the semi-reusable medicament assembly; and
storing, by the centralized system, the information related to the semi-reusable medicament assembly, wherein the centralized system includes at least one processor, and wherein the semi-reusable medicament assembly comprises a disposable drug delivery device and a reusable electronic module operatively coupled with the disposable drug delivery device.
58. The method of embodiment 57, the semi-reusable medicament assembly is configured to communicate with the centralized system via at least one wireless network.
59. The method of embodiment 58, wherein the at least one wireless network includes a cellular network.
60. The method of embodiment 57 or embodiment 58, wherein:
the centralized system includes a central database, and
the information communicated from the one or more information sources is stored in the central database.
61. The method of embodiment 57, wherein the one or more information sources include at least one of (i) a point of production of the semi-reusable medicament assembly, (ii) a point of distribution of the semi-reusable medicament assembly, (iii) a point of dispensation of the semi-reusable medicament assembly, and (iv) the reusable electronic module.
62. The method of embodiment 60, wherein the information related to the semi-reusable medicament assembly includes information identifying the semi-reusable medicament assembly, and wherein the method further comprises:
creating, by the centralized system, a medicament assembly record for the semi-reusable medicament assembly on the basis of the information identifying the semi-reusable medicament assembly, and storing the medicament assembly record in the central database.
63. The method of embodiment 62, wherein the creating includes:
linking, by the centralized system, an identity of the reusable electronic module to a medicament inside the operatively coupled drug delivery device.

64. The method of embodiment 62, wherein the information related to the semi-reusable medicament assembly further includes an identity of a patient associated with the semi-reusable medicament assembly, the patient identity being received from a point of dispensation of the semi-reusable medicament assembly, and wherein the method further comprises:
associating, by the centralized system, the medicament assembly record with the patient identity.
65. The method of embodiment 64, wherein the information related to the semi-reusable medicament assembly further includes logistics information received from a point of distribution of the semi-reusable medicament assembly.
66. The method of embodiment 64, wherein the associating includes:
linking the medicament assembly record to a patient record stored in the central database and containing the patient identity.
67. The method of embodiment 66, wherein the medicament assembly record is stored within the patient record.
68. The method of embodiment 67, further comprising:
creating, by the centralized system, the patient record.
69. The method of embodiment 64, wherein:
the information related to the semi-reusable medicament assembly further includes at least one of medicament information, logistics information, and drug delivery performance information, and
the centralized system is configured to store the at least one of medicament information, logistics information, and drug delivery performance information within the medicament assembly record.
70. The method of embodiment 69, wherein the medicament information includes at least one of a medicament name, a national drug code, a dosage, an expiration date, and a lot number.
71. The method of embodiment 57, wherein the reusable electronic module has a wireless connectivity capability to wirelessly communicate with the centralized system, and wherein the method further comprises:
activating, by the centralized system, a wireless connectivity in the reusable electronic module when a patient identity is associated with the semi-reusable medicament assembly, the patient identity received from a point of dispensation of the semi-reusable medicament assembly.
72. The method of embodiment 71, wherein activating the wireless connectivity enables the reusable electronic module to establish a wireless connection with a wireless network providing a relatively long range wireless coverage.
73. The method of embodiment 72, wherein the wireless network providing the relatively long range wireless coverage is a cellular network.
74. The method of embodiment 73, wherein the activating includes sending, by the centralized system, a provisioning request to a wireless carrier associated with the cellular network to activate the wireless connectivity in the reusable electronic module.
75. The method of embodiment 73, further comprising:
de-activating, by the centralized system, the wireless connectivity once information has been received that confirms an emptying of a medicament container in the semi-reusable medicament assembly.
76. The method of embodiment 75, wherein the de-activating includes sending, by the centralized system, a de-activation request to the wireless carrier associated with the cellular network to de-activate the wireless connectivity in the reusable electronic module.
77. The method of embodiment 57, wherein the one or more information sources include the reusable electronic module, the reusable electronic module being configured to wirelessly communicate with the centralized system and to collect information regarding a use of the disposable drug delivery device, and wherein the method further comprises:
wirelessly communicating at least a portion of a drug delivery performance information to the centralized system after a dosing event.
78. The method of embodiment 77, wherein the drug delivery performance information includes a timestamp of a dosing event and an amount of medicament in the disposable drug delivery device that is administered.
79. The method of embodiment 77, further comprising:
linking, by the centralized system, the drug delivery performance information to a medicament assembly record stored within a central database.
80. The method of embodiment 62, wherein:
the reusable electronic module can be recycled and coupled to a new disposable drug delivery device to form a new semi-reusable medicament assembly, and
the reusable electronic module is actively linked to only one semi-reusable medicament assembly at a time within the central database.
81. The method of embodiment 80, wherein the centralized system is configured to receive information related to a plurality of semi-reusable medicament assemblies, and to maintain a registry of active links between reusable electronic modules and respective semi-reusable medicament assemblies.
82. The method of embodiment 81, wherein the centralized system is further configured to inactivate and archive a past link associated with the reusable electronic module when a new active link between the reusable electronic module and the new semi-reusable medicament assembly is formed.
83. An embodiment for a method for tracking disposable drug delivery devices, the method comprising:
creating, by at least one processor, a medicament assembly record for a given semi-reusable medicament assembly in a central database remote from the given semi-reusable medicament assembly, wherein the given semi-reusable medicament assembly comprises a disposable drug delivery device and a reusable electronic module operatively coupled with the disposable drug delivery device, and wherein the medicament assembly record includes at least first information associating the disposable drug delivery device with the reusable electronic module.
84. The method of embodiment 83, further comprising:
receiving, by the at least one processor, second information regarding a dispensation of the semi-reusable medicament assembly, and associating the second information with the medicament assembly record in the central database.
85. The method of embodiment 84, wherein the second information includes an identity of a patient associated with the semi-reusable medicament assembly, and
associating the second information with the medicament assembly record in the central database includes associating the medicament assembly record with the patient identity.

86. The method of embodiment 84, further comprising:
receiving, by the at least one processor, third information regarding a distribution of the semi-reusable medicament assembly, and associating the third information with the medicament assembly record in the central database.
87. The method of embodiment 84, further comprising:
receiving, by the at least one processor, third information regarding a use of the semi-reusable medicament assembly, and associating the third information with the medicament assembly record in the central database.
88. The method of embodiment 87, wherein the third information includes drug delivery performance information of the disposable drug delivery device.
89. The method of embodiment 83, wherein the central database is configured to store a plurality of medicament assembly records, each medicament assembly record being created for a respective semi-reusable medicament assembly.
90. The method of embodiment 89, wherein two or more of the plurality of medicament assembly records include the same medicament identity information, and the method further comprises:
receiving, by the at least one processor, second information; and
associating the second information with each of the two or more of the plurality of medicament assembly records.
91. The method of embodiment 90, wherein the second information includes logistics information collected at a point of distribution of the semi-reusable medicament assembly.
92. The method of embodiment 83, further comprising:
receiving, by the at least one processor, second information regarding a distribution of the semi-reusable medicament assembly, and associating the second information with the medicament assembly record in the central database;
receiving, by the at least one processor, third information regarding a dispensation of the semi-reusable medicament assembly, and associating the second information with the medicament assembly record in the central database; and
receiving, by the at least one processor, fourth information regarding a use of the semi-reusable medicament assembly, and associating the third information with the medicament assembly record in the central database.
93. An embodiment for a centralized system for tracking disposable drug delivery devices, the centralized system comprising:
at least one processor;
a memory coupled with the at least one processor; and
program instructions that are stored in the memory and, when executed by the at least one processor, cause the at least one processor to receive, from one or more information sources, and store information related to at least one semi-reusable medicament assembly, the semi-reusable medicament assembly comprising a disposable drug delivery device and a reusable electronic module operatively coupled with the disposable drug delivery device.
94. The system of embodiment 93, further comprising a communication interface for communicating with the at least one semi-reusable medicament assembly.
95. The system of embodiment 94, wherein the communication occurs over a plurality of communication networks.
96. The system of embodiment 93, further comprising a central database, wherein the at least one processor stores the information related to the at least one semi-reusable medicament assembly in the central database.
97. The system of embodiment 93, wherein the at least one processor, the memory, and the program instructions are implemented in a cloud computing environment.

The invention claimed is:
1. A communication and tracking system for a drug delivery device comprising:
one or more servers having one or more processors configured to:
receive medicament information about a medicament in the drug delivery device at or after a point of production of the drug delivery device;
receive identification information of the drug delivery device;
link the identification information and the medicament information to a medicament assembly record; and
receive dispensation information that indicates that the drug delivery device has been dispensed to a patient;
a drug delivery device comprising:
an accelerometer;
a light sensor;
at least one performance sensor;
a primary container filled with a medicament;
a drive mechanism for delivering the medicament into a user;
a memory; and
one or more processors coupled to the memory, wherein the one or more processors are configured to:
determine, based on a first signal from the accelerometer, a movement of a packaging of the drug delivery device indicating a handling of the packaging by the user;
activate, in response to the determination that the drug delivery device has been handled by the user, the light sensor, wherein the light sensor is configured to indicate that the drug delivery device has been removed from the packaging of the drug delivery device;
determine, based on a second signal from the light sensor, that the drug delivery device has been removed from the packaging of the drug delivery device;
activate, in response to the determination that the drug delivery device has been removed from the packaging, the at least one performance sensor, wherein the at least one performance sensor is configured to indicate a dosing event of the drug delivery device, wherein the at least one performance sensor comprises (i) an initiation sensor positioned within the drug delivery device and configured to detect a start of the dosing event by detecting a pressure on a start switch sufficient to activate the drive mechanism, and (ii) a completion sensor positioned within the drug delivery device distal to the initiation sensor, wherein the completion sensor is configured to detect when the drive mechanism reaches a distalmost position upon completion of the dosing event;

determine, based on a third signal from the at least one performance sensor, that the dosing event of the drug delivery device has occurred; and send drug delivery performance information comprising information that the dosing event has occurred to the one or more servers, wherein the drug delivery performance information is sent via a long range wireless network, and wherein the one or more processors of the one or more servers are further configured to receive dispensation information comprising prescription information indicating that the drug delivery device has been prescribed to the patient.

2. The system of claim 1, wherein the identification information is encoded in a medicament label and/or an identification element.

3. The system of claim 1, wherein the identification information is encoded in at least an identification element comprising a radio frequency identification (RFID) tag.

4. The system of claim 1, wherein the one or more processors of the one or more servers are further configured to:
receive logistics information relating to the drug delivery device at a point of distribution; and
link the logistics information to the medicament assembly record.

5. The system of claim 1, wherein the one or more processors of the one or more servers are further configured to link, in response to receiving the dispensation information, a patient record to the medicament assembly record.

6. The system of claim 1, wherein the one or more processors of the one or more servers are further configured to update the medicament assembly record and a patient record to indicate that the dosing event has occurred.

7. The system of claim 1, wherein the at least one performance sensor is a vibration or acoustic sensor.

8. The system of claim 1, wherein the one or more servers is remote from the drug delivery device.

9. The system of claim 1, wherein the long range wireless network is a cellular network.

10. The system of claim 1, wherein:
the drug delivery device is one of a plurality of drug delivery devices in a medicament package;
each of the plurality of drug delivery devices in the medicament package has a unique electronic module identity, and the unique module identity of the drug delivery device is part of the identification information of the drug delivery device;
the medicament package has a unique electronic package identity; and
the one or more processors of the one or more servers are further configured to link each of the unique electronic module identities of the plurality of drug delivery devices to the unique electronic package identity.

11. A drug delivery apparatus comprising:
an accelerometer configured to indicate a handling of a packaging of the drug delivery apparatus by a user;
a light sensor configured to indicate that the drug delivery apparatus has been removed from the packaging of the drug delivery apparatus;
at least one performance sensor configured to indicate a dosing event of the drug delivery apparatus;
a primary container filled with a medicament;
a drive mechanism for delivering the medicament into the user;
a trigger for the user to activate the drive mechanism;
a power source configured to provide power to the one or more processors, the at least one activation sensor, and the at least one performance sensor;
a wireless transceiver configured to communicate over the long range wireless network;
a memory; and
one or more processors coupled to the memory, wherein the one or more processors are configured to:
determine, based on a first signal from the accelerometer, a movement of the packaging of the drug delivery apparatus indicating the handling of the packaging by the user;
activate, in response to the determination that the drug delivery apparatus has been handled by the user, the light sensor;
determine, based on a second signal from the light sensor, that the drug delivery apparatus has been removed from the packaging of the drug delivery apparatus;
activate, in response to the determination that the drug delivery apparatus has been removed from the packaging, the at least one performance sensor;
determine based on a third signal from the at least one performance sensor, that a dosing event of the drug delivery apparatus has occurred, wherein the at least one performance sensor comprises (i) an initiation sensor positioned within the drug delivery device and configured to detect a start of the dosing event by detecting a pressure on a start switch sufficient to activate the drive mechanism, and (ii) a completion sensor positioned within the drug delivery device distal to the initiation sensor, wherein the completion sensor is configured to detect when the drive mechanism reaches a distalmost position upon completion of the dosing event; and
send drug delivery performance information comprising information that the dosing event has occurred to a server, wherein the drug delivery performance information is sent via a long range wireless network.

12. The apparatus of claim 11, wherein the drug delivery performance information comprises at least one of a timestamp of a start of the dosing event and a timestamp of a completion of the dosing event.

13. The apparatus of claim 11, further comprising:
an electronic module comprising the power source, the wireless transceiver, the at least one activation sensor, and the at least one performance sensor; and
medicament delivery module comprising the primary container, the drive mechanism, and the trigger,
wherein the electronic module is configured to be coupled to the medicament delivery module.

14. The apparatus of claim 11, wherein the performance sensor is at least one of a pressure sensor, a vibration or acoustic sensor, and a light or proximity sensor.

15. The apparatus of claim 11, wherein the at least one performance sensor is activated only after the determination that the drug delivery apparatus has been removed from the packaging.

16. The system of claim 1, wherein the medicament information comprises at least one of a medicament name, a national drug code, a dosage, an expiration date, and a lot number.

* * * * *